(12) United States Patent
Chung et al.

(10) Patent No.: US 12,274,166 B2
(45) Date of Patent: Apr. 8, 2025

(54) PHOTOSENSITIVE MATERIAL AND PHOTODETECTOR INCLUDING THE SAME

(71) Applicant: POSTECH Research and Business Development Foundation, Pohang-Si (KR)

(72) Inventors: Dae Sung Chung, Pohang-si (KR); Ju Hee Kim, Pohang-si (KR)

(73) Assignee: Postech Research and Business Development Foundation

( * ) Notice: Subject to any disclaimer, the term of this patent is extended or adjusted under 35 U.S.C. 154(b) by 747 days.

(21) Appl. No.: 17/237,453

(22) Filed: Apr. 22, 2021

(65) Prior Publication Data

US 2022/0131084 A1    Apr. 28, 2022

(30) Foreign Application Priority Data

Oct. 27, 2020 (KR) .................. 10-2020-0140437

(51) Int. Cl.
| | |
|---|---|
| H10K 30/00 | (2023.01) |
| C07D 333/24 | (2006.01) |
| H10K 30/30 | (2023.01) |
| H10K 30/82 | (2023.01) |
| H10K 39/32 | (2023.01) |
| H10K 85/60 | (2023.01) |

(52) U.S. Cl.
CPC ......... *H10K 85/655* (2023.02); *C07D 333/24* (2013.01); *H10K 30/30* (2023.02); *H10K 30/451* (2023.02); *H10K 30/82* (2023.02); *H10K 39/32* (2023.02)

(58) Field of Classification Search
CPC .... H10K 85/655; H10K 30/30; H10K 30/451; H10K 30/82; H10K 39/32; C07D 333/24; C07D 333/06; C07D 409/10
See application file for complete search history.

(56) References Cited

U.S. PATENT DOCUMENTS

| | | |
|---|---|---|
| 7,355,775 B2 | 4/2008 | Yam et al. |
| 8,648,206 B2 | 2/2014 | Irie et al. |
| 9,343,601 B2 | 5/2016 | Choi et al. |
| 11,545,640 B2 * | 1/2023 | Guo ............... H10K 30/671 |

FOREIGN PATENT DOCUMENTS

| | | |
|---|---|---|
| JP | 2001-304955 A | 10/2001 |
| KR | 10-1430650 B1 | 8/2014 |

OTHER PUBLICATIONS

Nakahama et al "Tuning of Optical Properties and Thermal Cycloreversion Reactivity of Photochromic Diarylbenzene by Introducing Electron-Donating Substituents" J. Phys. Chem. C 2019, 123, 31212-31218. (Year: 2019).*

Chen et al. "Strategies for Designing Diarylethenes as Efficient Nonlinear Optical Switches" J. Phys. Chem. C 2014, 118, 4334-4345. (Year: 2014).*

Rad et al. "Spiropyran-based advanced photoswitchable materials: A fascinating pathway to the future stimuli-responsive devices" J. Photochem. Photobiol., C: Photochem. Rev. 2022, 51, 100487. (Year: 2022).*

Inagaki et al. "A Simple and Versatile Strategy for Rapid Color Fading and Intense Coloration of Photochromic Naphthopyran Families" J. Am. Chem. Soc. 2017, 139, 13429-13441. (Year: 2017).*

Fujita et al. "Photochromism of a Radical Diffusion-Inhibited Hexaarylbiimidazole Derivative with Intense Coloration and Fast Decoloration Performance" Org. Lett. 2008, 10, 3105-3108. (Year: 2008).*

Natali, M. and S. Giordani. "Molecular switches as photocontrollable "smart" receptors." *Chem. Soc. Rev.*, 2012, 41, 4010-4029.

Min Su Jang et al., "Spatial Confinement of the Optical Sensitizer to Realize a Thin Film Organic Photodetector with High Detectivity and Thermal Stability", The Journal of Physical Chemistry Letters, Lett. 2018, 9, 8-12.

Kyounghwan Kim et al., "Defect Restoration of Low-Temperature Sol-Gel-Derived ZnO via Sulfur Doping for Advancing Polyeric Schottky Photodiodes" Advanced Functional Materials, 2018, 28, 1802582.

Marcin Kielar et al., "Long-Term Stable Organic Photodetectors with Ultra Low Dark Currents for High Detectivity Applications" Scientific Reports, 2016, 6, 39201.

* cited by examiner

*Primary Examiner* — Amanda L. Aguirre
(74) *Attorney, Agent, or Firm* — Harness, Dickey & Pierce, P.L.C.

(57) ABSTRACT

Provided is a photosensitive material and a photodetector including the same. According to the present invention, the photodetector may include a photoactive layer having a photocurrent density of at most about $10^{-6}$ A/cm$^2$ under a first incidence condition, and having a photocurrent density of at least about $10^{-4}$ A/cm$^2$ under a second incidence condition. The wavelength of light under the second incidence condition is the same as the wavelength of light under the first incidence condition, and the intensity of light under the second incidence condition may be greater than the intensity of light under the first incidence condition.

11 Claims, 24 Drawing Sheets

PHOTOSENSITIVE MATERIAL AND PHOTODETECTOR INCLUDING THE SAME

CROSS-REFERENCE TO RELATED APPLICATIONS

This U.S. non-provisional patent application claims priority under 35 U.S.C. § 119 of Korean Patent Application No. 10-2020-0140437, filed on Oct. 27, 2020, the entire contents of which are hereby incorporated by reference.

BACKGROUND

The present disclosure herein relates to a photosensitive material and a photodetector including the same, and more particularly, to a photodetector having photodiode characteristics and photoconductor characteristics.

A photodetector is an element configured to transfer an optical signal to an electrical signal. A photodetector may include a photoactive layer. The photoactive layer may include a silicon-based photoactive layer and an organic material-based photoactive layer. The organic material-based photoactive layer may include a mixture of a p-type semiconductor material and an n-type semiconductor material. In this case, there is a limitation in that the photodetector exhibits high dark current characteristics. When the photosensitive layer of the photodetector includes any one of a p-type semiconductor and a n-type semiconductor, the external quantum efficiency of the photodetector is lowered.

SUMMARY

The present disclosure provides a photodetector having photodiode characteristics and photoconductor characteristics, and a photosensitive material used for the same.

The objects to be achieved herein are not limited to the above, and other objects not mentioned may be clearly understood by those skilled in the art from the following description.

The present disclosure herein relates to a photosensitive material and a photodetector including the same. According to an embodiment of the inventive concept, a photodetector may include a photoactive layer having a photocurrent density of at most about $10^{-6}$ A/cm$^2$ under a first incidence condition, and having a photocurrent density of at least about $10^{-4}$ A/cm$^2$ under a second incidence condition. The wavelength of light under the second incidence condition is the same as the wavelength of light under the first incidence condition, and the intensity of light under the second incidence condition may be greater than the intensity of light under the first incidence condition.

In an embodiment, the intensity of light under the first incidence condition may be at most about $10^{-3}$ W/cm$^2$.

In an embodiment, the photoactive layer may include an organic material and a photosensitive material. The photosensitive material may have: a first state represented by Chemical Formula 1; and a second state in which a carbon to which R$_3$ is bonded and a carbon to which R$_4$ is bonded are connected to each other to form a ring structure.

[Chemical Formula 1]

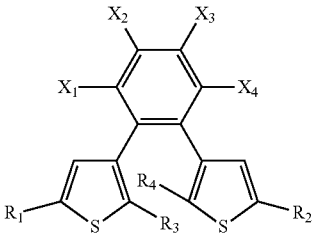

In Chemical Formula 1, R$_1$ and R$_2$ each independently include a substituted or unsubstituted aromatic ring compound of 5 to 20 carbon atoms, R$_3$ and R$_4$ are each independently an alkyl group of 1 to 3 carbon atoms, X$_1$, X$_2$, X$_3$, and X$_4$ are each independently hydrogen or a halogen element, and at least one of X$_1$, X$_2$, X$_3$, or X$_4$ includes a halogen element.

In an embodiment, a lowest unoccupied molecular orbital (LUMO) energy level of the photosensitive material in the second state may be different from a LUMO energy level of the photosensitive material in the first state.

In an embodiment, the LUMO energy level of the photosensitive material in the first state may be at least about $-3$ eV, the LUMO energy level of the photosensitive material in the second state may be less than about $-3$ eV, and the photosensitive material in the first state may have an absorption peak of at least about 300 nm.

In an embodiment, the photodetector may further include: a first electrode disposed on a first surface of the photoactive layer; and a second electrode disposed on a second surface of the photoactive layer, and the second surface of the photoactive layer may face the first surface.

In an embodiment, the photoactive layer and the first electrode forms a Schottky junction under the first incidence condition, and the photoactive layer and the first electrode forms an ohmic junction under the second incidence condition.

In an embodiment, a photoactive material may have: a first state represented by Chemical Formula 1, and a second state in which a carbon to which R$_3$ is bonded and a carbon to which R$_4$ is bonded, in the Chemical Formula 1, are connected to each other to form a ring structure; a lowest unoccupied molecular orbital (LUMO) energy level of at least about $-3$ eV and an absorption peak of at least about 300 nm in the first state; and a LUMO energy level of less than about $-3$ eV.

[Chemical Formula 1]

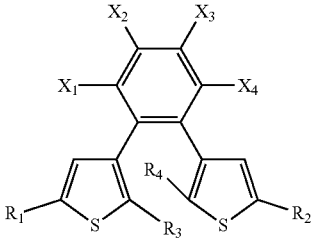

In Chemical Formula 1, R$_1$ and R$_2$ each independently include a substituted or unsubstituted aromatic ring compound of 5 to 20 carbon atoms, R$_3$ and R$_4$ are each independently an alkyl group of 1 to 3 carbon atoms, X$_1$, X$_2$, X$_3$, and $X_4$ are each independently hydrogen or a halogen element, and at least one of $X_1$, $X_2$, $X_3$, or $X_4$ includes a halogen element.

In an embodiment, the second state may be represented by the following chemical formula 2.

[Chemical Formula 2]

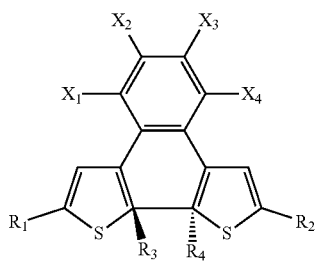

In Chemical Formula 2, $R_1$ and $R_2$ each independently are a substituted or unsubstituted aromatic ring compound of 5 to 20 carbon atoms, $R_3$ and $R_4$ are each independently an alkyl group of 1 to 3 carbon atoms, $X_1$, $X_2$, $X_3$, and $X_4$ are each independently hydrogen or a halogen element, and at least one of $X_1$, $X_2$, $X_3$, or $X_4$ includes a halogen element.

In an embodiment, $R_1$ and $R_2$ in the chemical formula 1 each independently may be a cyano (—CN)-substituted aromatic ring compound of 5 to 20 carbon atoms, or a halogen-substituted aromatic ring compound of 5 to 20 carbon atoms.

In an embodiment, a material represented by the Chemical Formula 1 may be represented by any one of Chemical Formula 1A, Chemical Formula 1B, and Chemical Formula 1D.

[Chemical Formula 1A]

[Chemical Formula 1B]

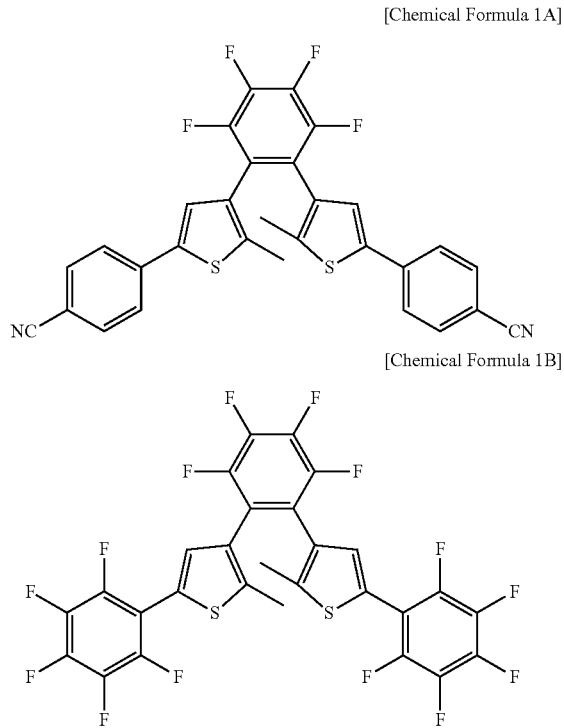

[Chemical Formula 1D]

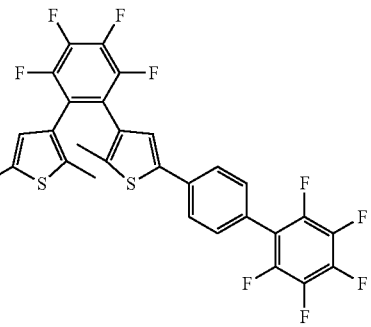

In an embodiment, a material represented by the Chemical Formula 1 may be represented by Chemical Formula 1C.

[Chemical Formula 1C]

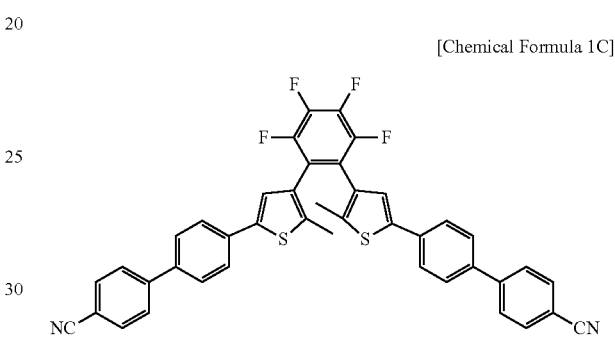

BRIEF DESCRIPTION OF THE FIGURES

The accompanying drawings are included to provide a further understanding of the inventive concept, and are incorporated in and constitute a part of this specification. The drawings illustrate exemplary embodiments of the inventive concept and, together with the description, serve to explain principles of the inventive concept. In the drawings.

DETAILED DESCRIPTION

Figure 1:
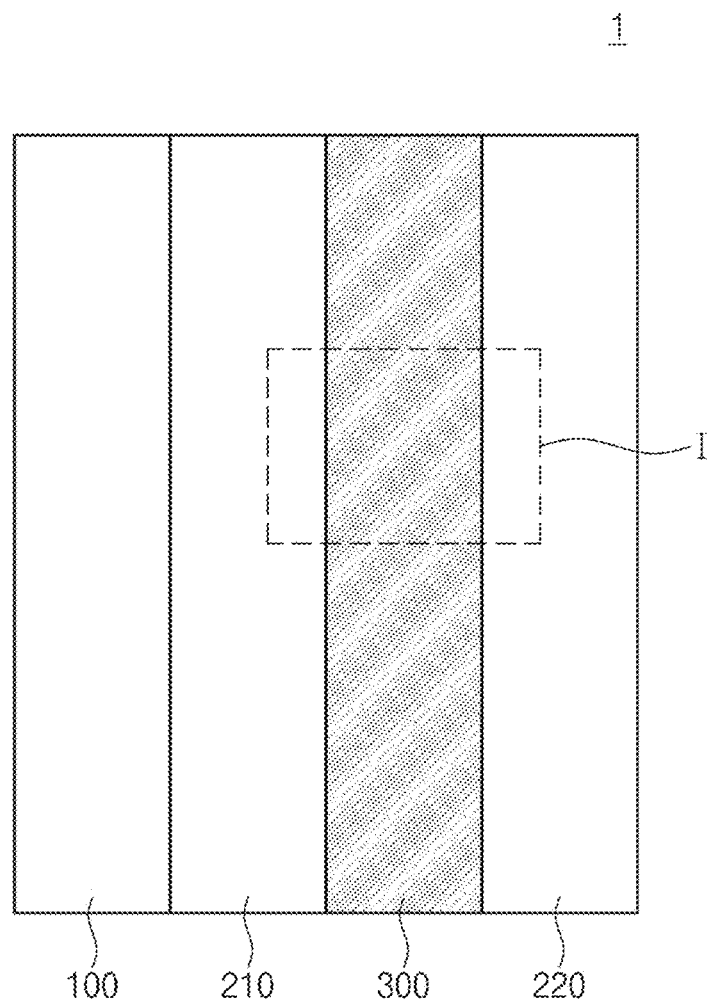
FIG. 1 is a diagram schematically illustrating a photodetector according to embodiments.

In order to fully understand the configuration and the effect of the inventive concept, preferred embodiments of the inventive concept will be described with reference to the accompanying figures. However, the inventive concept is not limited to the embodiments disclosed below, but may be implemented in various forms and various modifications may be added. However, it is provided to complete the disclosure of the inventive concept through the description of the present embodiments, and to fully inform the scope of the inventive concept to those of ordinary skill in the art. Those of ordinary skill in the art will understand that the inventive concept may be practiced in any suitable environment.

The terms used in the present specification are for describing exemplary embodiments, and are not intended to limit the inventive concept. In this specification, the singular form also includes the plural form unless specifically stated in the phrase. As used herein, 'comprises' and/or 'comprising' means that the recited material, component, step, operation and/or element are one or more other material, component, step, operation and/or element, or the presence or addition of material, component, step, operation and/or element is not excluded.

When a film (or layer) is referred to herein as being on another film (or layer) or substrate, it may be formed directly on another film (or layer) or substrate, or a third film (or layer) may be interposed.

In various embodiments of the present specification, terms such as first, second, and third are used to describe various regions, films (or layers), etc., but these regions and films are not limited by these terms. These terms are only used to distinguish one region or film (or layer) from another region or film (or layer). Accordingly, the film quality referred to as the first film quality in one embodiment may be referred to as the second film quality in another embodiment. Each embodiment described and illustrated herein also includes its complementary embodiment. Parts indicated by the same reference numerals throughout the specification represent the same components.

In addition, embodiments described in the present specification will be described with reference to cross-sectional views and/or plan views, which are ideal exemplary views of the inventive concept. In the drawings, thicknesses of films and regions are exaggerated for effective description of technical content. Therefore, the shape of the exemplary diagram may be modified by manufacturing technology and/or acceptable tolerance. Embodiments of the inventive concept are not limited to the specific form shown, but also include a change in form generated according to a manufacturing operation. For example, the etched region shown at a right angle may be rounded or may have a shape having a predetermined curvature. Accordingly, the regions illustrated in the drawings have schematic properties, and the shape of the regions illustrated in the drawings are intended to illustrate a specific shape of the device region and are not intended to limit the scope of the inventive concept.

In the present specification, an alkyl group may be a linear alkyl group, a branched alkyl group, or a cyclic alkyl group. The number of carbon atoms of an alkyl group is not particularly limited, but may be an alkyl group having 1 to 3 carbon atoms. Examples of an alkyl group include, but are not limited to, a methyl group, an ethyl group, and a propyl group. An aromatic ring compound may be monocyclic or polycyclic. The number of carbon atoms of an aromatic ring compound may be 5 or more and 20 or less, but is not limited thereto. Examples of an aromatic ring compound include, but are not limited to, a phenyl group, a biphenyl group, a naphthyl group, and/or a fluorenyl group.

In the present specification, examples of a halogen element may be fluorine (F), chlorine (Cl), bromine (Br), and iodine (I), etc., but are not limited thereto.

In the present specification, "substituted or unsubstituted" may mean substituted or unsubstituted with one or more substituents selected from the group consisting of a hydrogen atom, a deuterium atom, a halogen element, an ether group, a halogenated alkyl group, a halogenated alkoxy group, a halogenated ether group, an alkyl group, a cyano group, a cyano-substituted alkyl group, a cyano-substituted aryl group, a cyano-substituted aromatic ring group, and a hydrocarbon ring group. In addition, each of the substituents exemplified above may be substituted or unsubstituted. For example, the biphenyl group may be interpreted as an aryl group, or a phenyl group substituted with a phenyl group.

Unless otherwise defined in the chemical formula of the present specification, it may be indicated that when a chemical bond is not drawn at a position where a chemical bond is to be drawn, a hydrogen atom is bonded at the position.

In the present specification, the same reference symbol throughout the entire text may indicate the same component.

Hereinafter, a photosensitive material and a photodetector including the same according to the inventive concept will be described.

Figure 2:
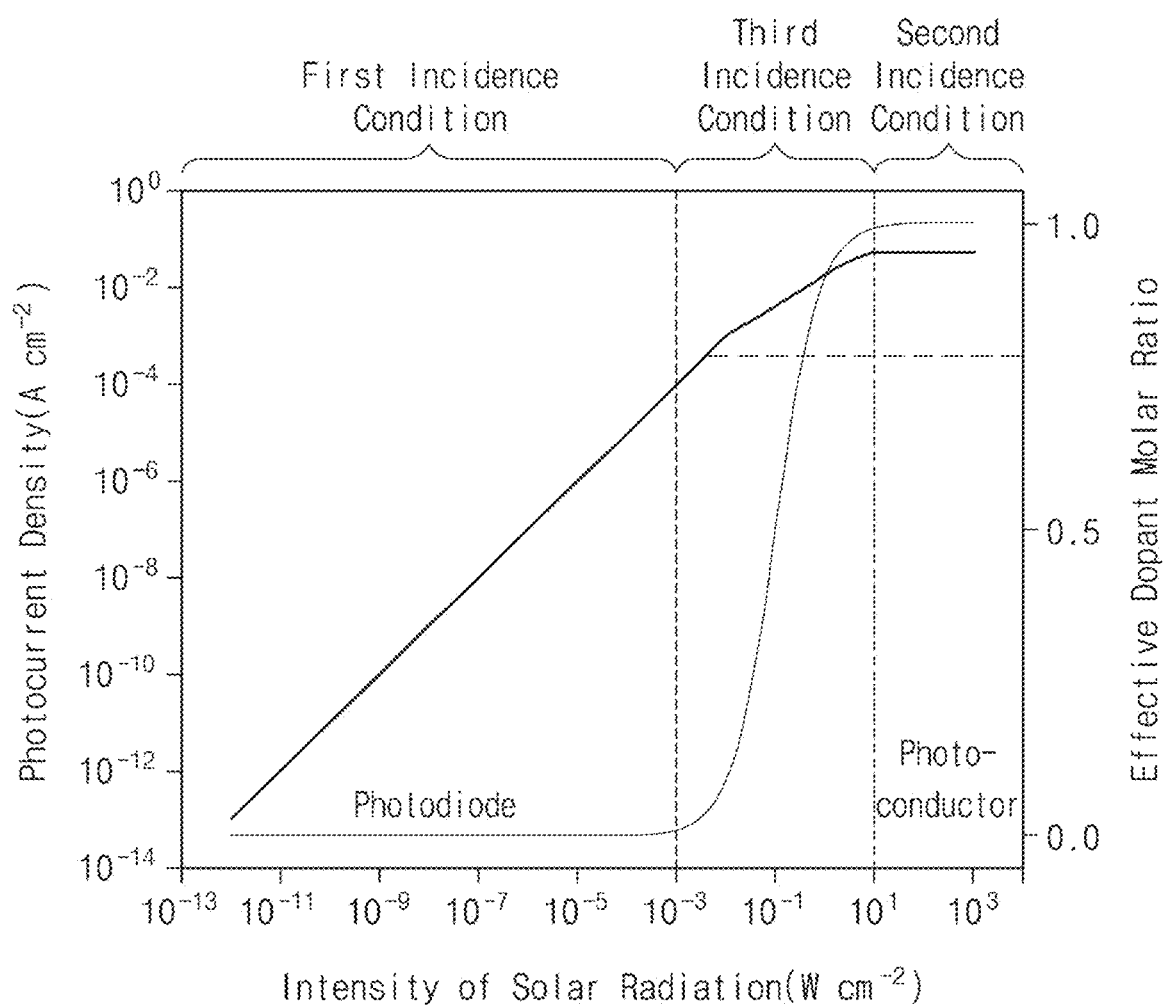
FIG. 2 is a graph showing a photocurrent density and an effective dopant molar ratio according to the solar radiation intensity of a photoactive layer.

FIG. 1 is a diagram schematically illustrating a photodetector according to embodiments. FIG. 2 is a graph showing a photocurrent density and an effective dopant molar ratio according to the solar radiation intensity of a photoactive layer.

Referring to FIGS. 1 and 2, a photodetector 1 may include a substrate 100, a first electrode 210, a photoactive layer 300, and a second electrode 220. For example, the substrate 100 may include a semiconductor substrate (for example, a silicon substrate), an organic substrate, or an inorganic substrate (for example, a glass substrate). However, a material of the substrate 100 is not limited thereto. The first electrode 210 may be disposed on the substrate 100. The first electrode 210 may include a metal, doped polycrystalline silicon, or a conductive polymer. The second electrode 220 may be disposed on the first electrode 210, and may be separated from the first electrode 210. A voltage applied to the second electrode 220 may be different from a voltage applied to the first electrode 210. One of a first electrode 210 and a second electrode 220 may be an anode, and the other may be a cathode. At least one of a first electrode 210 or a second electrode 220 may be a transparent electrode. For example, when light is incident through the substrate 100, the substrate 100 and the first electrode 210 may be transparent. When light is incident through the second electrode 220, the second electrode 220 may be a transparent electrode.

The photoactive layer 300 may be disposed between the first electrode 210 and the second electrode 220. For example, the photoactive layer 300 may have a first surface and a second surface facing each other. The first electrode 210 may be disposed on the first surface of the photoactive layer 300, and the second electrode 220 may be disposed on the second surface of the photoactive layer 300. The photoactive layer 300 may include an organic semiconductor material, and a photosensitive material. The organic semiconductor material may have a conductivity type. For example, the organic semiconductor material may be a p-type organic semiconductor material. The organic semiconductor material may be a polymer. For example, the organic semiconductor material may include polythiophene and/or a derivative thereof, polyfluorene and/or a derivative thereof, and/or a combination thereof. The photosensitive material may function as a photosensitive dopant according to an incidence condition. The content of the photosensitive material in the photoactive layer 300 may be less than the content of the organic semiconductor material. The photosensitive material may include diarylethene and/or a diarylethene derivative. For example, the photosensitive material may have a first state and a second state. The photosensitive material may be in the first state under a first incidence condition. The photosensitive material in the first state may have a structure in an open form. The photosensitive material in the first state may be represented by the following Chemical Formula 1.

[Chemical Formula 1]

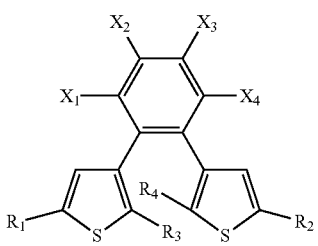

In Chemical Formula 1, $R_1$ and $R_2$ each independently include a substituted or unsubstituted aromatic ring compound having 5 to 20 carbon atoms, $R_3$ and $R_4$ are each independently an alkyl group having 1 to 3 carbon atoms, $X_1$, $X_2$, $X_3$, and $X_4$ are each independently hydrogen or a halogen element, and at least one of $X_1$, $X_2$, $X_3$, or $X_4$ includes a halogen element.

According to an embodiment, at least one of $X_1$, $X_2$, $X_3$, or $X_4$ in Chemical Formula 1 may include a fluorine element.

According to an embodiment, each of $X_1$, $X_2$, $X_3$, and $X_4$ in Chemical Formula 1 may include a fluorine element.

According to an embodiment, $R_1$ and $R_2$ are each independently a cyano (—CN)-substituted aromatic ring compound or a halogen-substituted aromatic ring compound.

According to an embodiment, each of $R_1$ and $R_2$ is a fluorine-substituted aromatic ring compound.

A material represented by Chemical Formula 1 may include a material represented by the following Chemical Formula 1-1.

[Chemical Formula 1-1]

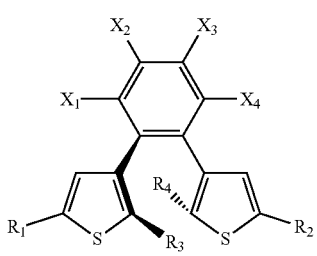

In Chemical Formula 1-1, $R_1$, $R_2$, $R_3$, $R_4$, $X_1$, $X_2$, $X_3$, and $X_4$ are the same as defined in Chemical Formula 1.

A material represented by Chemical Formula 1 may be represented by any one of Chemical Formula 1A, Chemical Formula 1B, Chemical Formula 1C, and Chemical Formula 1D.

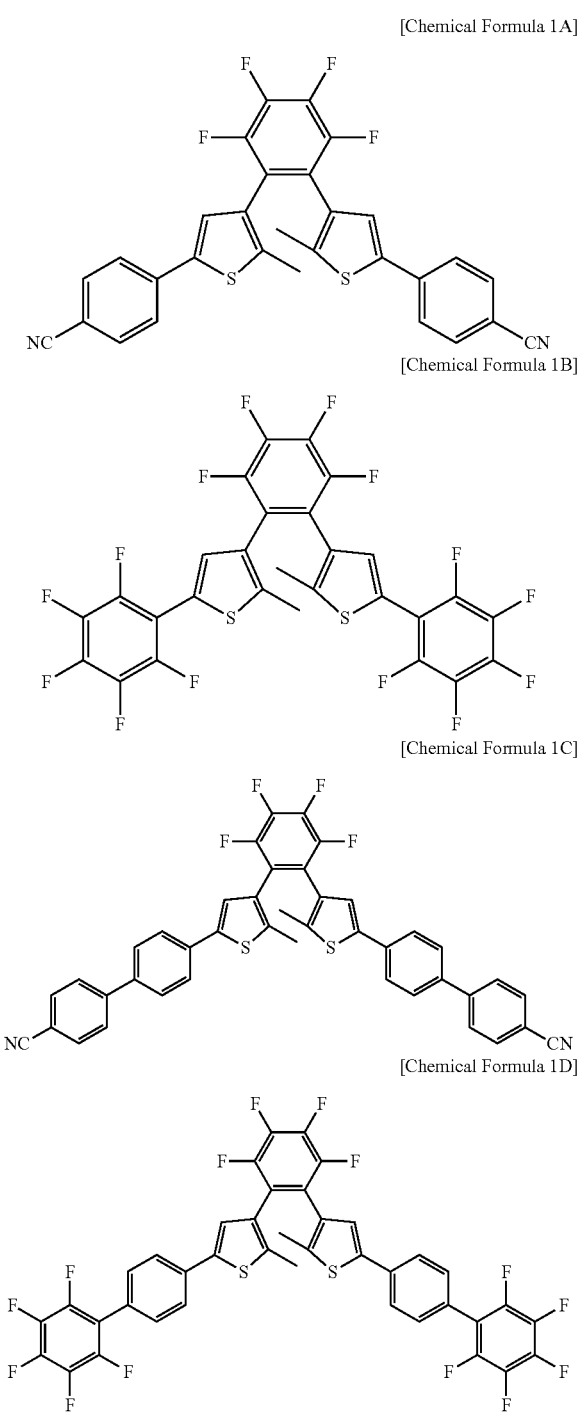

[Chemical Formula 1A]

[Chemical Formula 1B]

[Chemical Formula 1C]

[Chemical Formula 1D]

Light may be incident onto the photodetector 1. The light may include ultraviolet rays, visible rays, and near-infrared rays. The light may be derived from solar radiation. In the present specification, unless otherwise limited, light may mean white light or natural light.

The first incidence condition may mean that light having a relatively weak intensity is incident onto the photoactive layer 300. For example, solar radiation of at most about $10^{-3}$ W/cm$^2$ (solar radiation same or less than $10^{-3}$ W/cm$^2$) may be applied to the photoactive layer 300 under the first incidence condition as shown in FIG. 2. Applying solar radiation may mean applying white light or natural light.

The photosensitive material in the first state may have a lowest unoccupied molecular orbital (LUMO) energy level of at least about −3 eV. For example, the photosensitive material in the first state may have a LUMO energy level same or greater than −3 eV. Accordingly, the photoactive layer 300 may function as a photodiode. For example, the photoactive layer 300 may have a photocurrent density of at most about $10^{-6}$ A/cm$^2$ under the first incidence condition. The photosensitive material in the first may have a photocurrent density same or less than $10^{-6}$ A/cm$^2$ under the first incidence condition. The photoactive layer 300 may exhibit low dark current characteristics under the first incidence condition.

The photosensitive material in the first state may have an absorption peak of at least about 300 nm. For example, a material represented by Chemical Formula 1 may have an absorption peak of at least about 300 nm in the first state. The photosensitive material in the first state may absorb not only ultraviolet rays but also visible rays. According to some embodiments, the photosensitive material in the first state may have an absorption peak of at least about 350 nm. For example, a material represented by Chemical Formula 1C and a material represented by Chemical Formula 1D may have an absorption peak of at least about 350 nm.

When the intensity of light increases, the photosensitive material in the first state may be converted into a photosensitive material in a second state. Here, the light may be white light or natural light as described above.

The photosensitive material may be in a second state under a second incidence condition. The wavelength of light under the second incidence condition may be the same as the wavelength of light under the first incidence condition. The intensity of light under the second incidence condition may be greater than the intensity of light under the first incidence condition. In other words, the second incidence condition may be a bright condition as a direct sunlight condition. Solar radiation of at least about $10^1$ W/cm$^2$ may be applied to the photoactive layer 300 under the second incidence condition. The photosensitive material in the second state may have an isomeric relationship with the photosensitive material in the first state. The second state may be a closed form or a ring structure. The photosensitive material in the second state may have a structure in which in Chemical Formula 1, the carbon to which $R_3$ is bonded and the carbon to which $R_4$ is bonded are connected to each other to form a ring structure. The photosensitive material in the second state may be represented by Chemical Formula 2

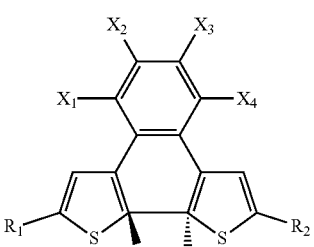

[Chemical Formula 2]

In Chemical Formula 2, $R_1$, $R_2$, $R_3$, $R_4$, $X_1$, $X_2$, $X_3$, and $X_4$ are the same as defined in Chemical Formula 1. For example, in Chemical Formula 2, $R_1$ and $R_2$ each independently include a substituted or unsubstituted aromatic ring compound having 5 to 20 carbon atoms, $R_3$ and $R_4$ are each independently an alkyl group having 1 to 3 carbon atoms, $X_1$, $X_2$, $X_3$, and $X_4$ are each independently hydrogen or a halogen element, and at least one of $X_1$, $X_2$, $X_3$, or $X_4$ includes a halogen element.

The conjugation length of the photosensitive material in the second state may be longer than the conjugation length of the photosensitive material in the first state. The LUMO energy level of the photosensitive material in the second state may be smaller than the LUMO energy level of the photosensitive material in the first state. The photosensitive material in the second state may have a LUMO energy level of less than about −3 eV. The photoactive layer 300 may function as a photoconductor. For example, the photoactive layer 300 may have a photocurrent density of at least about $10^{-4}$ A/cm$^2$ under the second incidence condition. For example, the photoactive layer 300 may have a photocurrent density same or greater than $10^{-4}$ A/cm$^2$ under the second incidence condition.

According to embodiments, the photosensitive material may include an alkyl thienyl group, so that the photosensitive material in the second state may have a low LUMO energy level (for example, a LUMO energy level of less than about −3 eV). Furthermore, the photosensitive material may include an alkyl thienyl group, so that the photosensitive material may have an absorbance for ultraviolet and near-ultraviolet light.

In case of using a general photosensitive dopant, even if the intensity of light increases by at least about $10^1$ W/cm$^2$, it may be difficult to achieve a photocurrent density of greater than $10^{-3}$ A/cm$^2$. In other words, when the intensity of light is greater than a specific range, a photocurrent density may get saturated, and exhibit a constant value. This may make it difficult for the photosensitive layer 300 to function as a photoconductor.

When the intensity of light increases as shown in FIG. 2, an effective dopant molar ratio may increase. The effective dopant molar ratio may mean number of moles of a photosensitive material in the second state with respect to number of moles of the total photosensitive material in the photoactive layer 300. When light having an intensity of at least about $10^1$ W/cm$^2$ is applied to the photoactive layer 300 (second incidence condition), an effective dopant molar ratio increases and the photoactive layer 300 may have a photocurrent density of at least about $10^{-4}$ A/cm$^2$. The photoactive layer 300 may function as a photoconductor.

According to embodiments, the photoactive layer 300 may have a linear dynamic range (LDR). Therefore, the photodetector 1 may detect objects under not only a dark condition but also a direct sunlight condition.

The photoactive layer 300 may be in a co-existing state under a third incidence condition. The wavelength of light under the third incidence condition may be substantially the same as the wavelength of light under the first incidence condition, and the wavelength of light under the second incidence condition. The intensity of light under the third incidence condition may be greater than the intensity of light under the first incidence condition, and may be smaller than the intensity of light under the second incidence condition. For example, solar radiation of more than about $10^{-3}$ W/cm$^2$ and less than about $10^1$ W/cm$^2$ may be applied to the photoactive layer 300 under the third incidence condition. The photoactive layer 300 under the third incidence condition may include a photosensitive material in the first state and a photosensitive material in the second state.

The photosensitive material in the photoactive layer 300 may be a solid.

The photodetector 1 according to embodiments may be an image sensor.

Figure 3A:
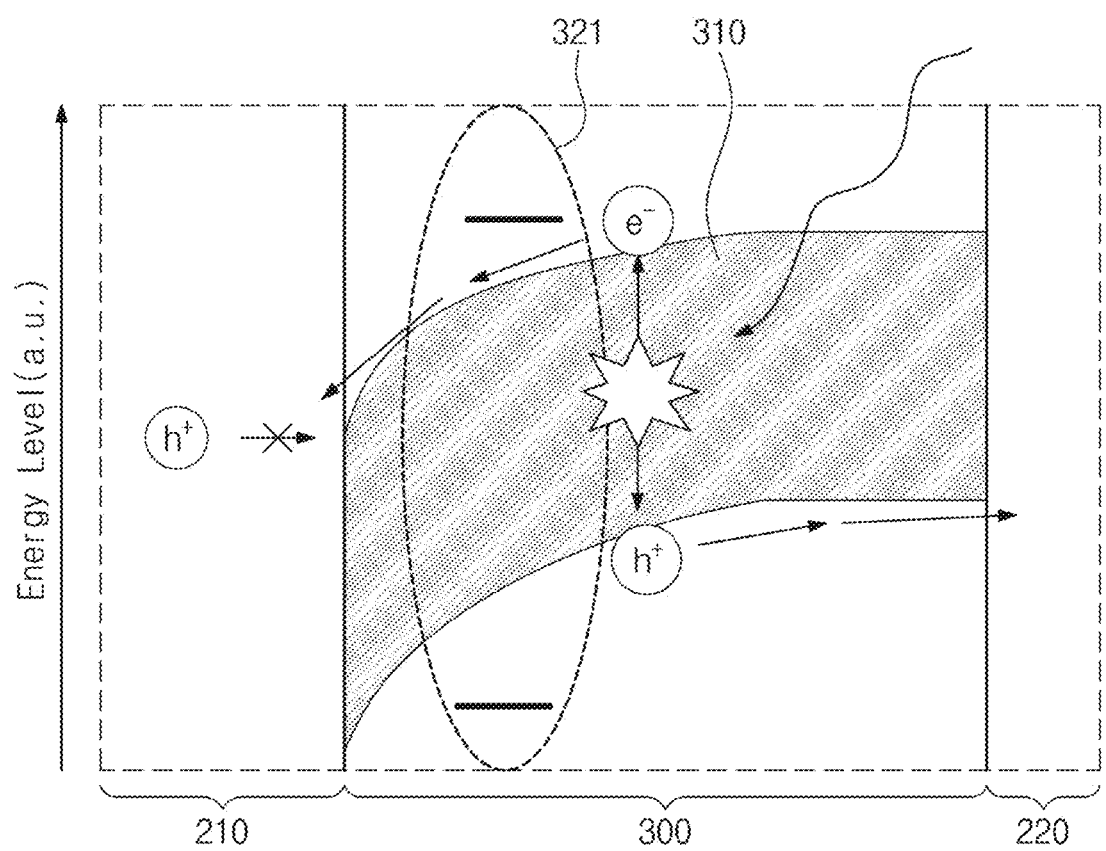
FIG. 3A is a diagram for explaining the energy levels and operating principles of an organic semiconductor and a photosensitive material under a first incidence condition.
Figure 3B:
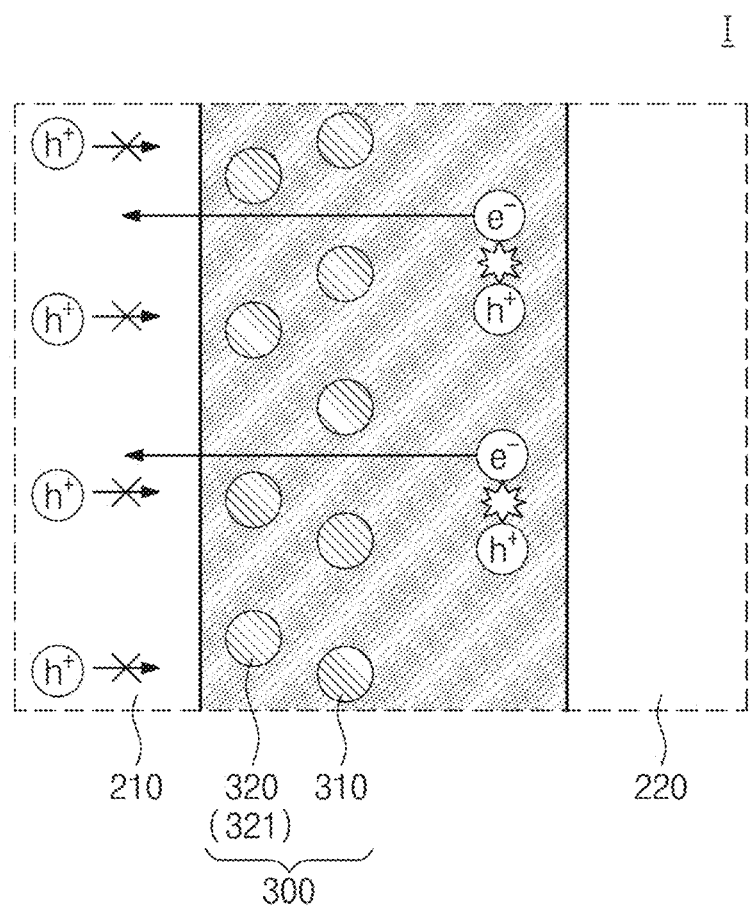
FIG. 3B is a diagram for explaining the operation of a photodetector under the first incidence condition, and is an enlarged view of area I of FIG. 1.

FIG. 3A is a diagram for explaining the energy levels and operating principles of an organic semiconductor and a photosensitive material under the first incidence condition. FIG. 3B is a diagram for explaining the operation of a photodetector under the first incidence condition, and is an enlarged view of area I of FIG. 1. FIGS. 3A and 3B are now described with reference to FIGS. 1 and 2 together.

Referring to FIGS. 3A, and 3B, the photoactive layer 300 may include an organic semiconductor material 310 and a photosensitive material 320 under the first incidence condition. The photosensitive material 320 may be the photosensitive material 321 in the first state. Light may be incident onto the photoactive layer 300. The light may cause exciton dissociation in an organic semiconductor material 310. Accordingly, electrons (e$^-$) and holes (h$^+$) may be generated. The organic semiconductor material 310 may be involved in movement of electrons (e$^-$). Electrons (e$^-$) in the photoactive layer 300 may move to the first electrode 210, and holes (h$^+$) in the photoactive layer 300 may move to the second electrode 220. The photosensitive material 321 in the first state may have a relatively short conjugation length. Due to the energy level of the photosensitive material 321 in the first state, the photosensitive material 321 in the first state may not have an effect on the movement of electrons. In other words, during operation of the photodetector, the photoactive layer 300 may use one kind (p-type) of the organic semiconductor material 310. The first electrode 210 and the photoactive layer 300 may form a Schottky junction. It may be difficult for holes (h$^+$) in the first electrode 210 to be transferred into the photoactive layer 300. The photodetector may function as a photodiode.

The photosensitive material 321 in the first state may have a gain of more than zero and less than one. The gain may be calculated with the following Mathematical Equation 1.

$$\text{Gain} = \frac{\chi \tau \mu V}{L^2} \qquad \text{[Mathematical Equation 1]}$$

In Mathematical Equation 1, $\chi$ an exciton dissociation ratio and is less than one. V is an applied bias (unit: V), $\tau$ is a carrier lifetime (unit: s), $\mu$ is a carrier mobility (unit: cm$^2$/Vs), and L is a film thickness.

Figure 4A:
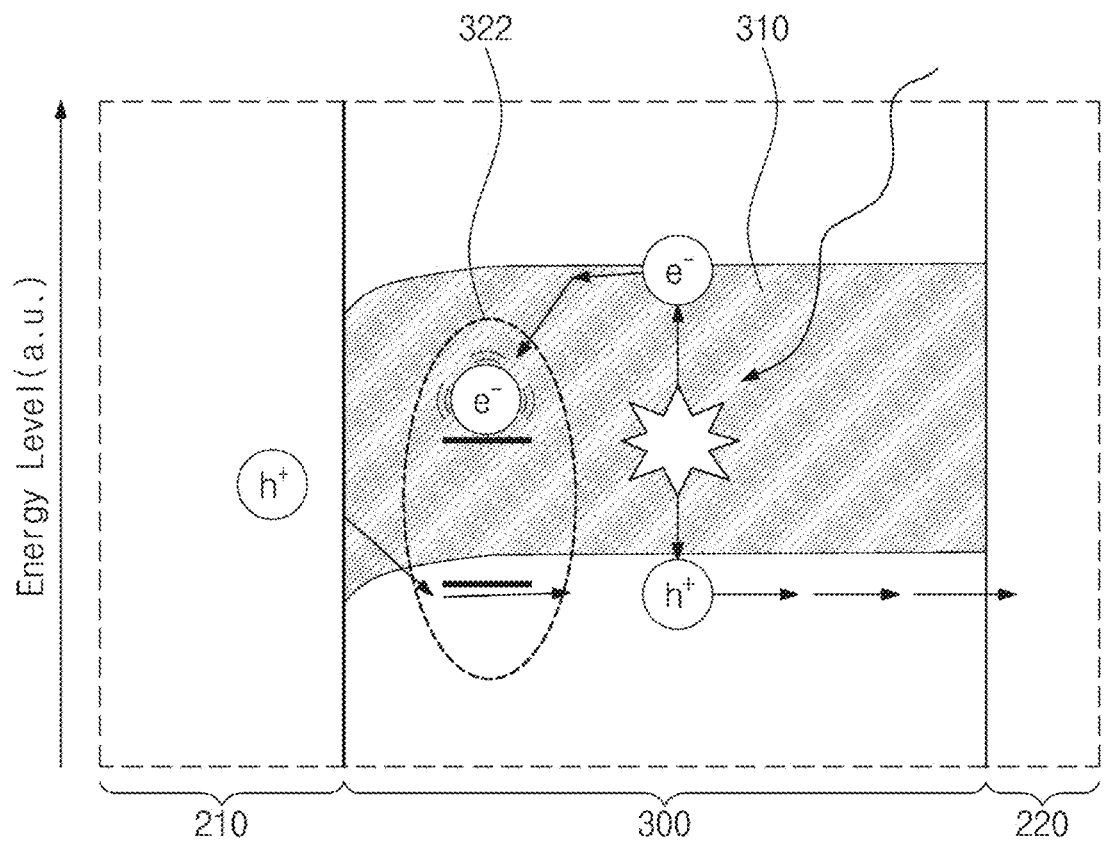
FIG. 4A is a diagram for explaining the energy levels and operating principles of an organic semiconductor and a photosensitive material under a second incidence condition.
Figure 4B:
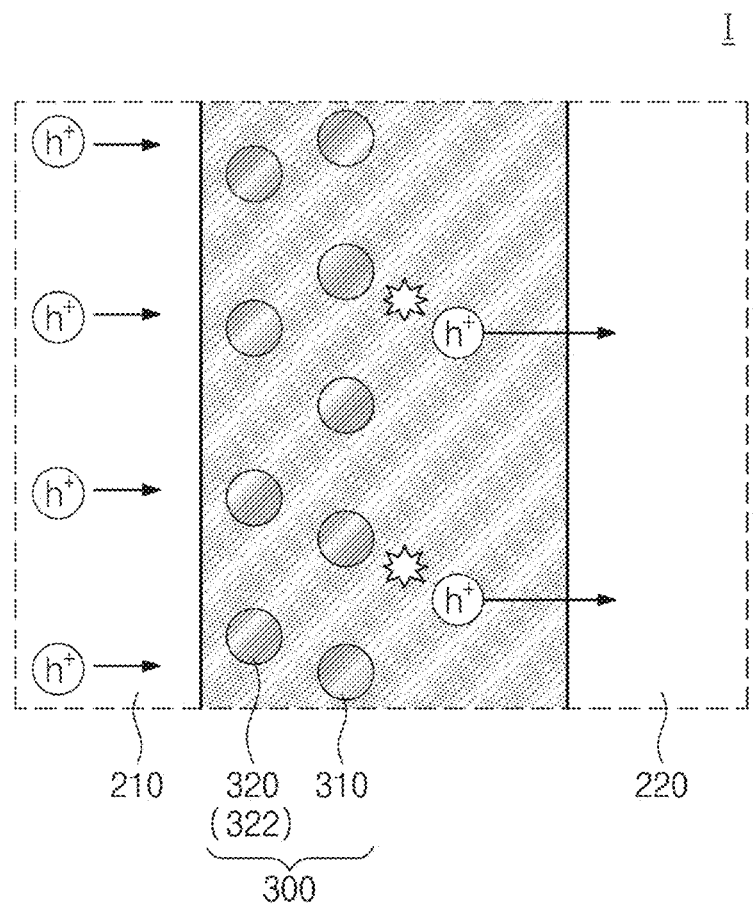
FIG. 4B is a diagram for explaining the operation of a photodetector under a second incidence condition, and is an enlarged view of area I of FIG. 1.

FIG. 4A is a diagram for explaining the energy levels and operating principles of an organic semiconductor and a photosensitive material under the second incidence condition. FIG. 4B is a diagram for explaining the operation of the photodetector under the second incidence condition, and is an enlarged view of area I of FIG. 1.

Referring to FIG. 4A and FIG. 4B, the photoactive layer 300 may include an organic semiconductor material 310 and a photosensitive material 320 under the second incidence condition. The photosensitive material 320 may include a photosensitive material 322 in the second state. The photosensitive material 322 in the second state may have a relatively long conjugation length. The energy level of the photosensitive material 322 in the second state may be different from the energy level of the photosensitive material 321 in the first state as described in FIG. 3A. The photosensitive material 322 in the second state may form a heterojunction with the organic semiconductor material 310. The heterojunction may be a type-II staggered heterojunction. The photosensitive material 322 in the second state may function as a dopant. The photoactive layer 300 may be actuated using a p-type semiconductor material and an n-type dopant. The p-type semiconductor material may be the organic semiconductor material 310. The photosensitive material 322 in the second state may function as an n-type dopant.

The light may cause exciton dissociation in the organic semiconductor material 310. Holes ($h^+$) and electrons ($e^-$) may be generated due to the exciton dissociation, the electrons ($e^{31}$) may be trapped by the photosensitive material 322 in the second state. In other words, the photosensitive material 322 in the second state may be involved in movement of electrons ($e^-$). Hole ($h^+$) in the photoactive layer 300 may move to the second electrode 220. Due to the energy level of the photosensitive material 322 in the second state, holes ($h^+$) in the first electrode 210 may move to the photoactive layer 300. The photosensitive material 322 in the second state may be involved in movement of holes ($h^+$) in the first electrode 210.

The first electrode 210 and the photoactive layer 300 may form an ohmic junction. The photodetector may function as a photoconductor.

The photosensitive material 322 in the second state may have a gain of at least about 1 to at most about 1000. The gain may be calculated with Mathematical Equation 1 above. The photosensitive material 322 in the second state has a gain of at least about 1, so that the photoactive layer 300 may have a current density of at least about $10^{-4}$ A/cm$^2$, and the photodetector may function as a photoconductor.

Figure 5:
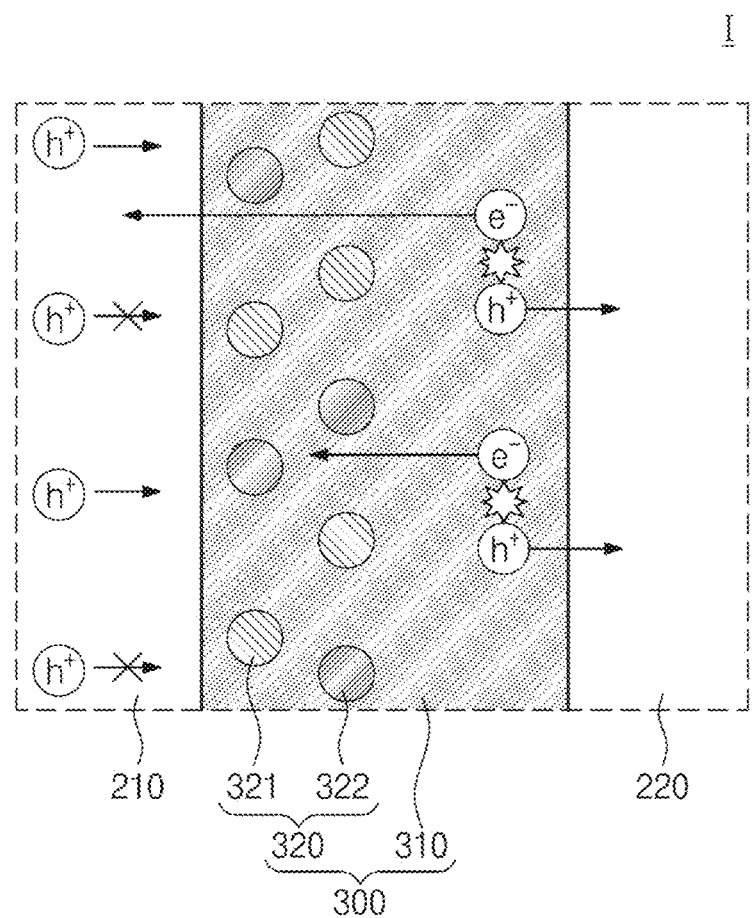
FIG. 5 is a diagram for explaining the operation of a photodetector under a third incidence condition, and is an enlarged view of area I of FIG. 1.

FIG. 5 is a diagram for explaining the operation of a photodetector under a third incidence condition, and is an enlarged view of area I of FIG. 1. FIG. 5 is now described with reference to FIGS. 1 and 2 together.

Figure 6:
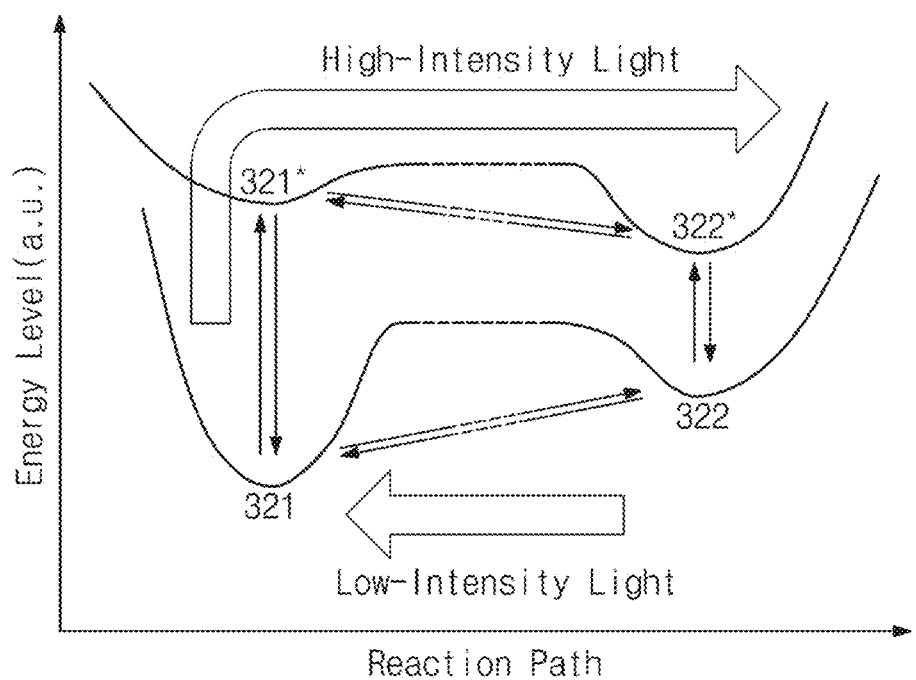
FIG. 6 is a diagram for explaining conversion reactions of a photosensitive material in a first state and a photosensitive material in a second state according to embodiments.

FIG. 6 is a diagram for explaining conversion reactions of a photosensitive material in a first state and a photosensitive material in a second state according to embodiments, and a diagram illustrating an energy level a photosensitive material versus a reaction path.

Referring to FIG. 6, a conversion reaction between the photosensitive material 321 in the first state and the photosensitive material 322 in the second state may be controlled according to the intensity of light. The conversion reaction between the photosensitive material 321 in the first state and the photosensitive material 322 in the second state may be represented by the following Reaction Formula 1. When high-intensity light is incident onto the photosensitive material 321 in the first state, the photosensitive material 321 in the first state may be converted into the photosensitive material 322 in the second state. For example, by radiating the photosensitive material with the high-intensity light, an excited photosensitive material 322* in the second state may be formed from the photosensitive material 321 in the first state via an excited photosensitive material 321* in the first state. The photosensitive material 322 in the second state may be formed from the excited photosensitive material 322* in the second state.

When the intensity of light decreases and low-intensity light is incident onto the photosensitive material 322 in the second state, the photosensitive material 322 in the second state may change to the photosensitive material 321 in the first state.

[Reaction Formula 1]

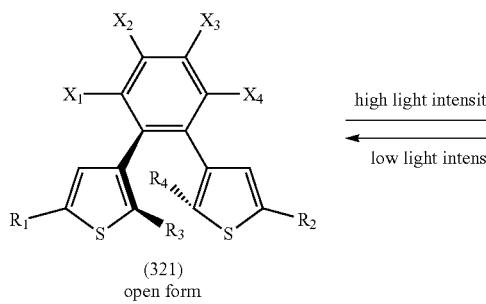

(321)
open form

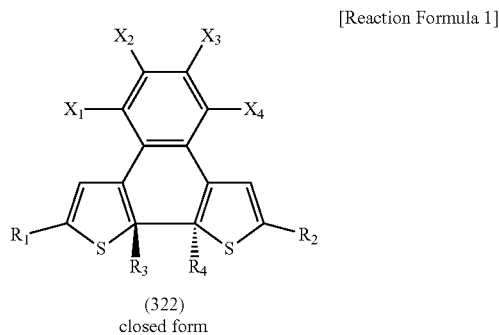

(322)
closed form

Referring to FIG. 5, the photoactive layer 300 under the third incidence condition may include an organic semiconductor material 310 and a photosensitive material 320. The photoactive layer 300 under the third incidence condition may be in a co-existing state. For example, the photosensitive material 320 may include a photosensitive material 321 in the first state and a photosensitive material 322 in the second state.

A plurality of holes ($h^{30}$) and a plurality of electrons ($e^-$) may be generated due to exciton dissociation. One of the plurality of electrons ($e^-$) may be trapped in the photosensitive material 322 in the second state and thus may not be transferred to the first electrode 210. Another one of the plurality of electrons ($e^-$) may be transferred to the first electrode 210. The photosensitive material 321 in the first state may not be involved in movement of the other electron ($e^-$). One of the plurality of holes ($h^+$) in the first electrode 210 may not move to the photosensitive material 300. Another one of the plurality of holes ($h^+$) in the first electrode 210 may be transferred to the photoactive layer 300.

In Reaction Formula 1, $R^1$, $R_2$, $R_3$, $R_4$, $X_1$, $X_2$, $X_3$, and $X_4$ are the same as defined in Chemical Formula 1. 321 means the photosensitive material in the first state, and 322 means the photosensitive material in the second state.

When the photosensitive material includes a cyclopentene group and the cyclopentene group is connected to two alkyl thienyl groups, the speed of conversion from the photosensitive material 322 in the second state to the photosensitive material 321 in the first state may not be high enough.

According to embodiments, the photosensitive material may include a halogen-substituted benzene ring. For example, as shown in Chemical Formula 1, Chemical Formula 2, and Reaction Formula 1, the photosensitive material may include a benzene ring, and at least one of $X_1$, $X_2$, $X_3$, or $X_4$ may include a halogen element. The benzene ring may be bonded to two alkyl thienyl groups. Accordingly, the photosensitive material 322 in the second state may be rapidly converted into the photosensitive material 321 in the first state. The conversion between the photosensitive material 321 in the first state and the photosensitive material 322 in the second state may be a cycloreversion.

Figure 7A:
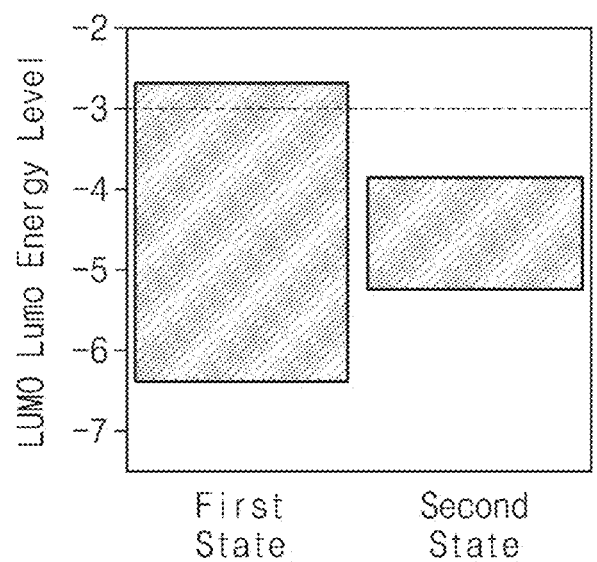
FIG. 7A is a result obtained by analyzing LUMO energy levels of a material, represented by Chemical Formula 1A, in a first state and in a second state.

FIG. 7A is a result obtained by analyzing LUMO energy levels (unit: eV) of a material, represented by Chemical Formula 1A, in a first state and in a second state.

Referring to FIG. 7A, the material, represented by Chemical Formula 1A, in the first state has a LUMO energy of at least about −3 eV. The material, represented by Chemical Formula 1A, in the second state has a LUMO energy of less than about −3 eV.

Figure 7B:
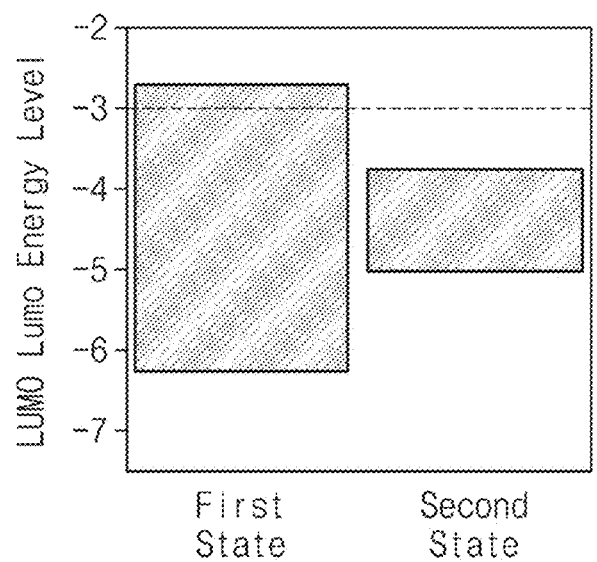
FIG. 7B is a result obtained by analyzing LUMO energy levels of a material, represented by Chemical Formula 1B, in a first state and in a second state.

FIG. 7B is a result obtained by analyzing LUMO energy levels (unit: eV) of a material, represented by Chemical Formula 1B, in a first state and in a second state.

Referring to FIG. 7B, the material, represented by Chemical Formula 1B, in the first state has a LUMO energy of at least about −3 eV. The material, represented by Chemical Formula 1B, in the second state has a LUMO energy of less than about −3 eV.

Figure 7C:
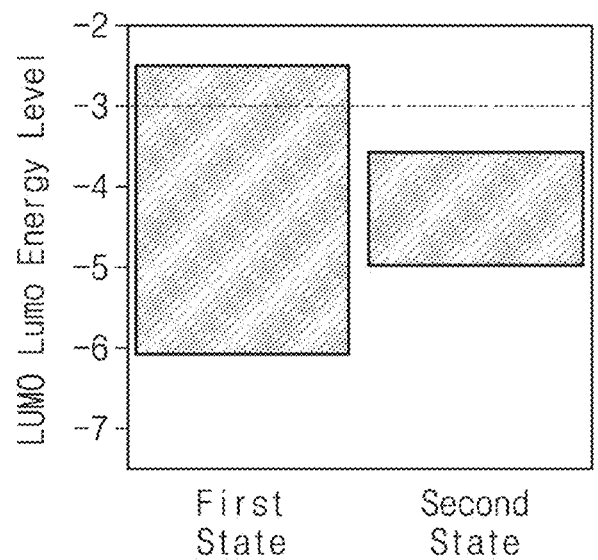
FIG. 7C is a result obtained by analyzing LUMO energy levels of a material, represented by Chemical Formula 1C, in a first state and in a second state.

FIG. 7C is a result obtained by analyzing LUMO energy levels (unit: eV) of a material, represented by Chemical Formula 1C, in a first state and in a second state.

Referring to FIG. 7C, the material, represented by Chemical Formula 1C, in the first state has a LUMO energy of at least about −3 eV. The material, represented by Chemical Formula 1C, in the second state has a LUMO energy of less than about −3 eV.

Figure 7D:
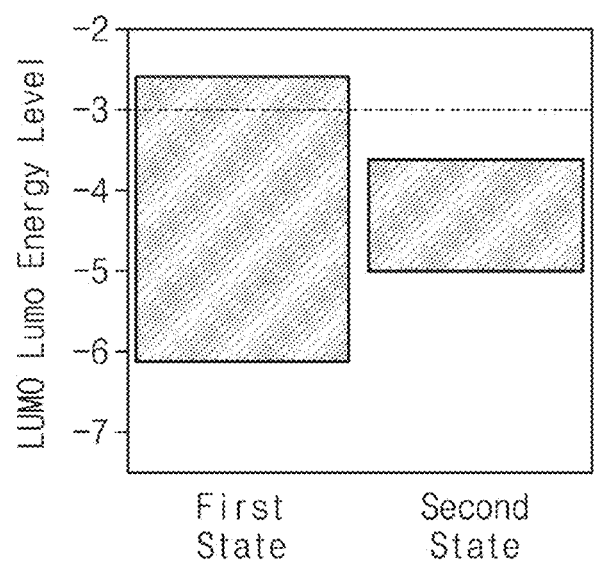
FIG. 7D is a result obtained by analyzing LUMO energy levels of a material, represented by Chemical Formula 1D, in a first state and in a second state.

FIG. 7D is a result obtained by analyzing LUMO energy levels (unit: eV) of a material, represented by Chemical Formula 1D, in a first state and in a second state.

Referring to FIG. 7D, the material, represented by Chemical Formula 1D, in the first state has a LUMO energy of at least about −3 eV. The material, represented by Chemical Formula 1D, in the second state has a LUMO energy of less than about −3 eV.

Figure 8A:
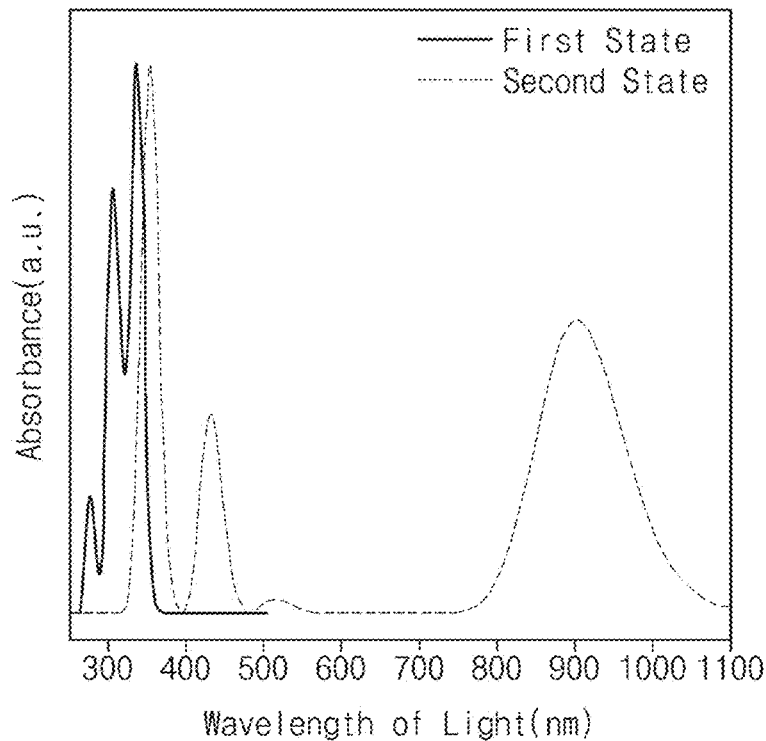
FIG. 8A is a graph showing the absorbance of a material represented by Chemical Formula 1A versus the wavelength of light.

FIG. 8A is a graph showing the absorbance of a material represented by Chemical Formula 1A versus the wavelength of light. The absorbance is analyzed for each of the first state and the second state.

Referring to FIG. 8A, the material, represented by Chemical Formula 1A, in the first state has an absorption peak for light having a wavelength of at least about 300 nm. The absorbance of the material, represented by Chemical Formula 1A, in the first state according to the wavelength of light may be different from the absorbance of the material in the second state according to the wavelength of light.

Figure 8B:
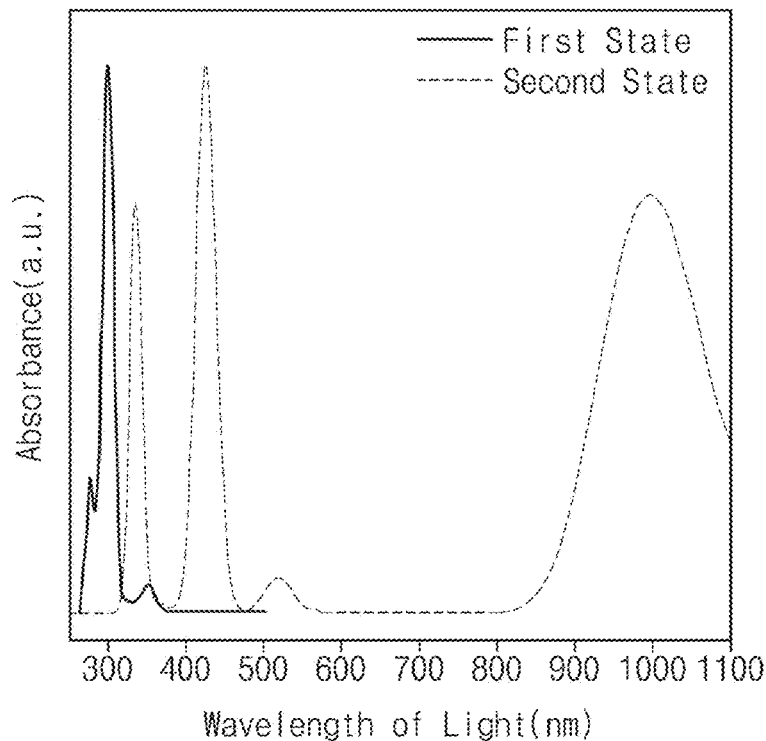
FIG. 8B is a graph showing the absorbance of a material represented by Chemical Formula 1B versus the wavelength of light.

FIG. 8B is a graph showing the absorbance of a material represented by Chemical Formula 1B versus the wavelength of light. The absorbance is analyzed for each of the first state and the second state.

Referring to FIG. 8B, the material, represented by Chemical Formula 1B, in the first state has an absorption peak for light having a wavelength of at least about 300 nm.

Figure 8C:
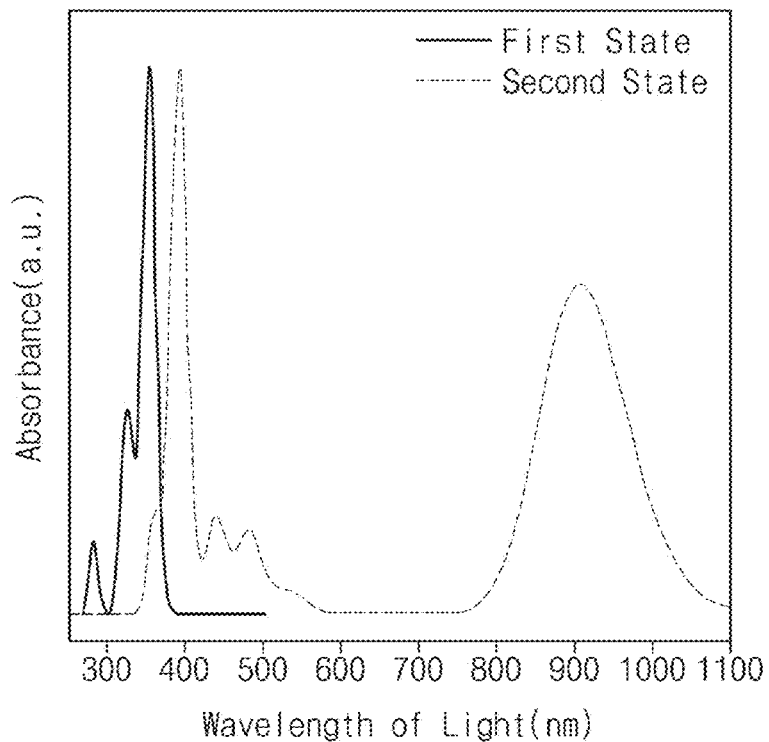
FIG. 8C is a graph showing the absorbance a material represented by Chemical Formula 1C versus the wavelength of light.

FIG. 8C is a graph showing the absorbance of a material represented by Chemical Formula 1C versus the wavelength of light. The absorbance is analyzed for each of the first state and the second state.

Referring to FIG. 8C, the material, represented by Chemical Formula 1C, in the first state has an absorption peak for light having a wavelength of at least about 300 nm, in particular, at least about 350 nm.

Figure 8D:
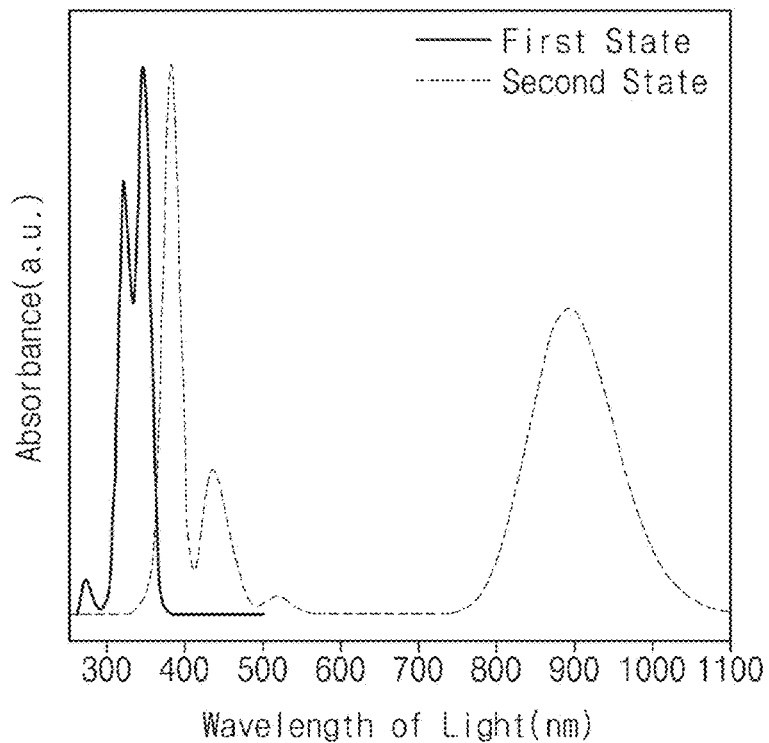
FIG. 8D is a graph showing the absorbance of a material represented by Chemical Formula 1D versus the wavelength of light.

FIG. 8D is a graph showing the absorbance of a material represented by Chemical Formula 1D versus the wavelength of light. The absorbance is analyzed for each of the first state and the second state.

Referring to FIG. 8D, the material, represented by Chemical Formula 1D, in the first state has an absorption peak for light having a wavelength of at least about 300 nm, in particular, at least about 350 nm.

Figure 9:
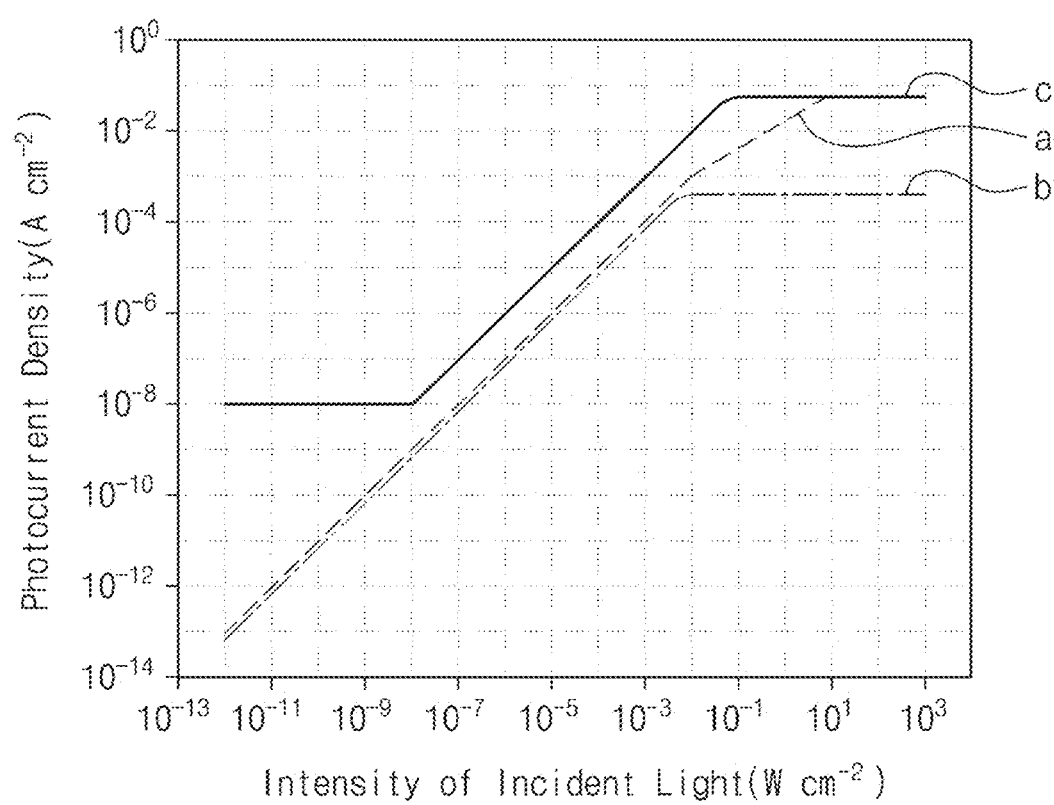
FIG. 9 is a graph showing the photocurrent densities of a photodiode, a photoconductor and a photodetector according to embodiments versus the intensity of incident light.

FIG. 9 is a graph showing the photocurrent densities of a photodiode, a photoconductor and a photodetector according to embodiments versus the intensity of incident light. a shows a result of a photodetector according to embodiments, b shows a result of a photodiode, and c shows a result of a photoconductor.

Referring to FIG. 9, when the intensity of incident light is small (for example, the intensity of incident light same or less than about $10^{-3}$ W/cm$^2$), the value of the photocurrent density of the photodiode versus the intensity of incident light may show a linear function. When the intensity of incident light is same or greater than about $10^{-3}$ W/cm$^2$, for example same or greater than about $10^{-2}$ W/cm$^2$, the photocurrent density of the photodiode may be saturated, and may have a constant value.

When the intensity of incident light is about $10^{-3}$ W/cm$^2$ to about $10^{-1}$ W/cm$^2$, the graph of a function regarding the photocurrent density of the photoconductor versus the intensity of incident light may be linear. When the intensity of incident light is equal to or less than about $10^{-8}$ W/cm$^2$, the photocurrent density of the photoconductor versus the intensity of incident light may be constant.

Under a condition that the range of incident light is about $10^{-12}$ W/cm$^2$ to about $10^1$ W/cm$^2$, the graph of a function regarding the photocurrent density of the photodetector according to embodiments versus the intensity of incident light may be linear. When the intensity of incident light is small (for example, the intensity of incident light of at most $10^{-3}$ W/cm$^2$), the photocurrent density of the photodetector may be proportional to the intensity of incident light. The value of the photocurrent density of the photodetector versus the intensity of incident light may show a linear function. When the intensity of light is about $10^{-3}$ W/cm$^2$, the graph of a function regarding the photocurrent density of the photodetector versus the intensity of incident light may be the same as or similar to the graph of the function regarding the photocurrent density of the photodiode versus the intensity of incident light. Even if the intensity of incident light is equal to or greater than about $10^{-3}$ W/cm$^2$, the graph of the function regarding the photocurrent density of the photodetector according to embodiments versus the intensity of incident light may be linear.

Figure 10A:
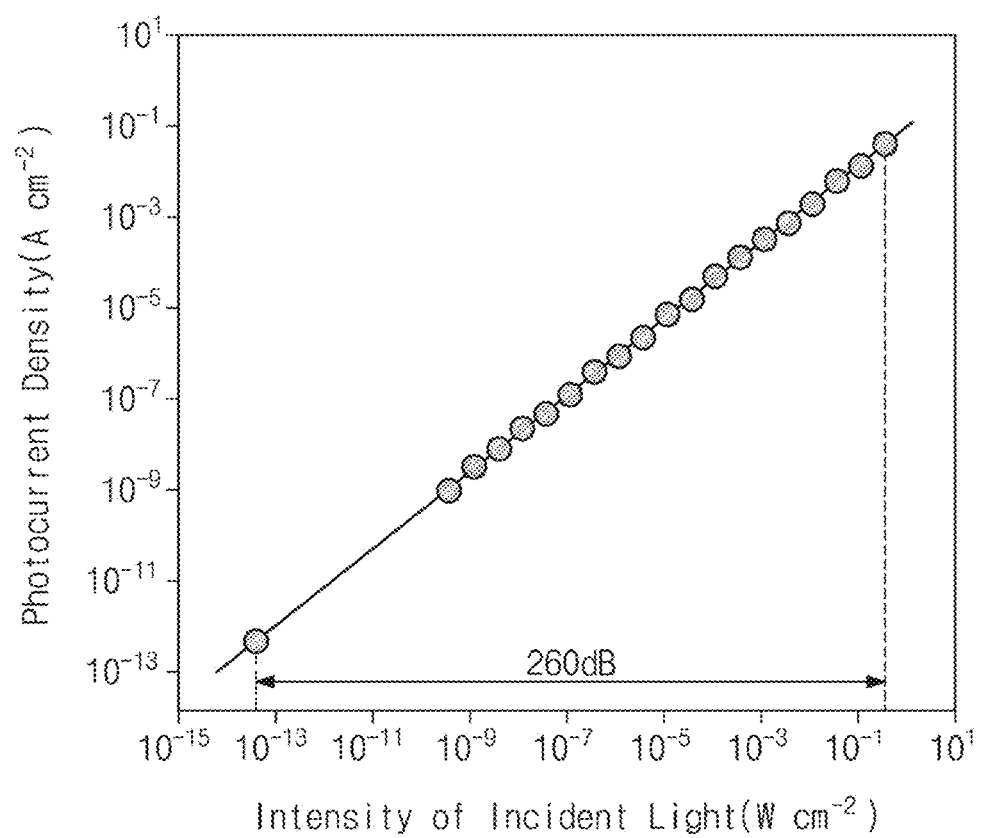
FIG. 10A is a graph showing the photocurrent density of a photodetector including a blue selective photoactive layer versus the intensity of solar radiation.
Figure 10B:
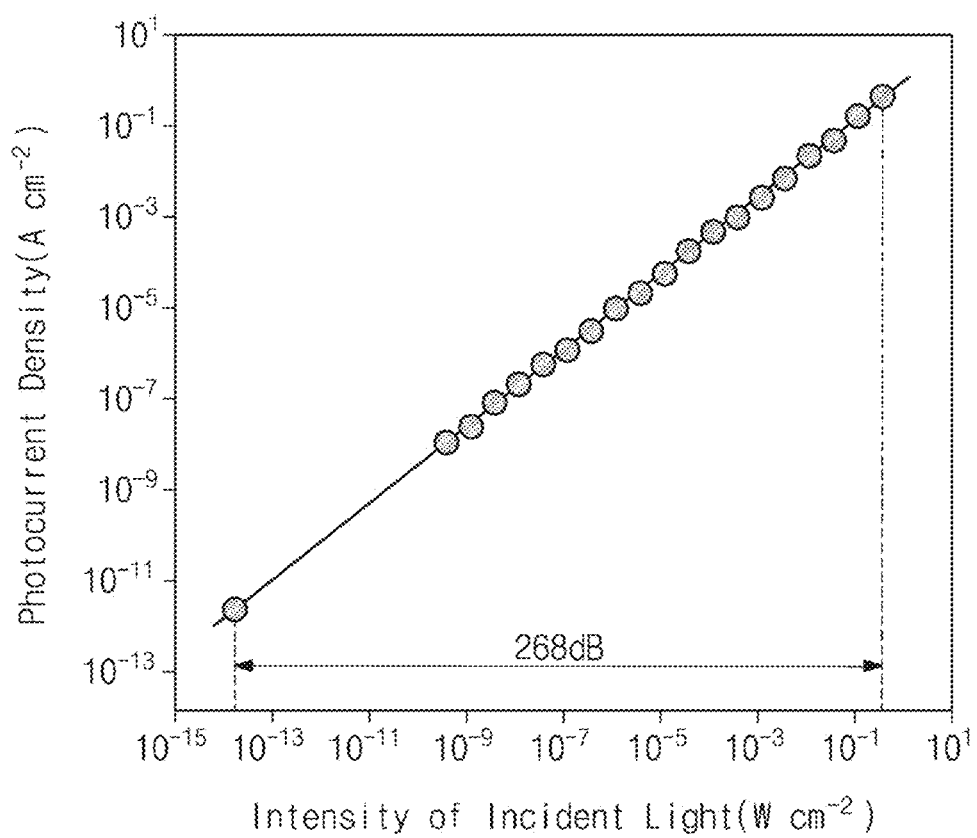
FIG. 10B is a graph showing the photocurrent density of a photodetector including a green selective photoactive layer versus the intensity of solar radiation.
Figure 10C:
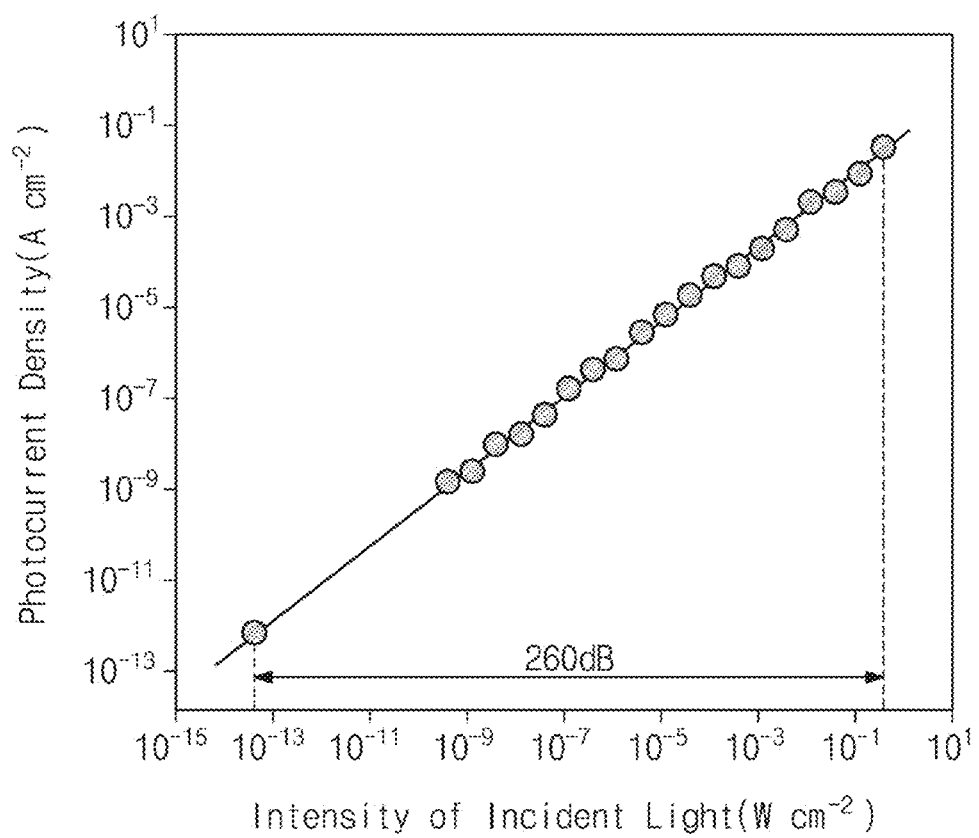
FIG. 10C is a graph showing the photocurrent density of a photodetector including a red selective photoactive layer versus the intensity of solar radiation.
Figure 10D:
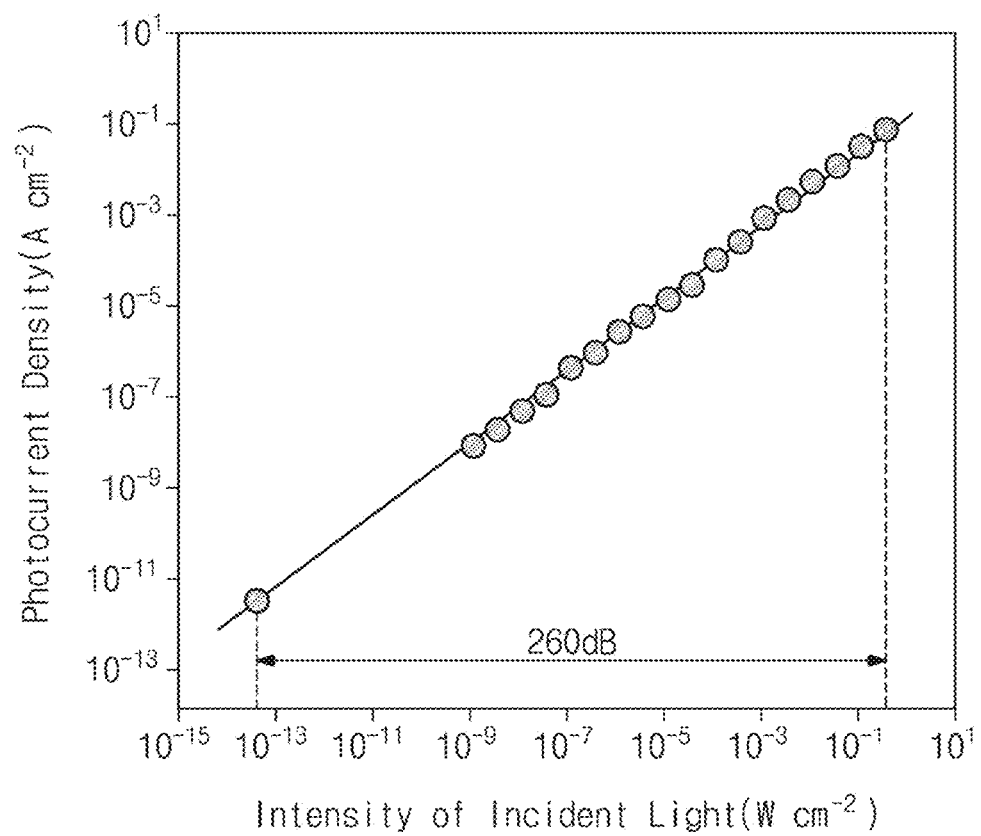
FIG. 10D is a graph showing the photocurrent density of a photodetector including a near-infrared selective photoactive layer versus the intensity of solar radiation.

FIG. 10A is a graph showing the photocurrent density of the photodetector including a blue selective photoactive layer versus the intensity of solar radiation. FIG. 10B is a graph showing the photocurrent density of the photodetector including a green selective photoactive layer versus the intensity of solar radiation. FIG. 10C is a graph showing the photocurrent density of the photodetector including a red selective photoactive layer versus the intensity of solar radiation. FIG. 10D is a graph showing the photocurrent density of the photodetector including a near-infrared selective photoactive layer versus the intensity of solar radiation. Here, the blue selective photoactive layer may include a photosensitive material and a blue selective organic semiconductor material. The green selective photoactive layer may include a photosensitive material and a green selective organic semiconductor material. The red selective photoactive layer may include a photosensitive material and a red selective organic semiconductor material. The near-infrared selective photoactive layer may include a photosensitive material and a near-infrared selective organic semiconductor material.

Referring to FIG. 10A, the photodetector including the blue selective photoactive layer may show a linear function regarding the photocurrent density value versus the intensity of solar radiation. Here, the intensity of solar radiation may be about $10^{-13}$ W/cm$^2$ to about $10^{-1}$ W/cm$^2$.

Referring to FIG. 10B, the photodetector including the green selective photoactive layer may show a linear function regarding the photocurrent density value versus the intensity of solar radiation. Here, the intensity of solar radiation may be about $10^{-13}$ W/cm$^2$ to about $10^{-1}$ W/cm$^2$.

Referring to FIG. 10C, the photodetector including the red selective photoactive layer may show a linear function regarding the photocurrent density value versus the intensity of solar radiation. Here, the intensity of solar radiation may be about $10^{-13}$ W/cm$^2$ to about $10^{-1}$ W/cm$^2$.

Referring to FIG. 10D, the photodetector including the near-infrared selective photoactive layer may show a linear function regarding the photocurrent density value versus the intensity of solar radiation. Here, the intensity of solar radiation may be about $10^{-13}$ W/cm$^2$ to about $10^{-1}$ W/cm$^2$.

Figure 11:
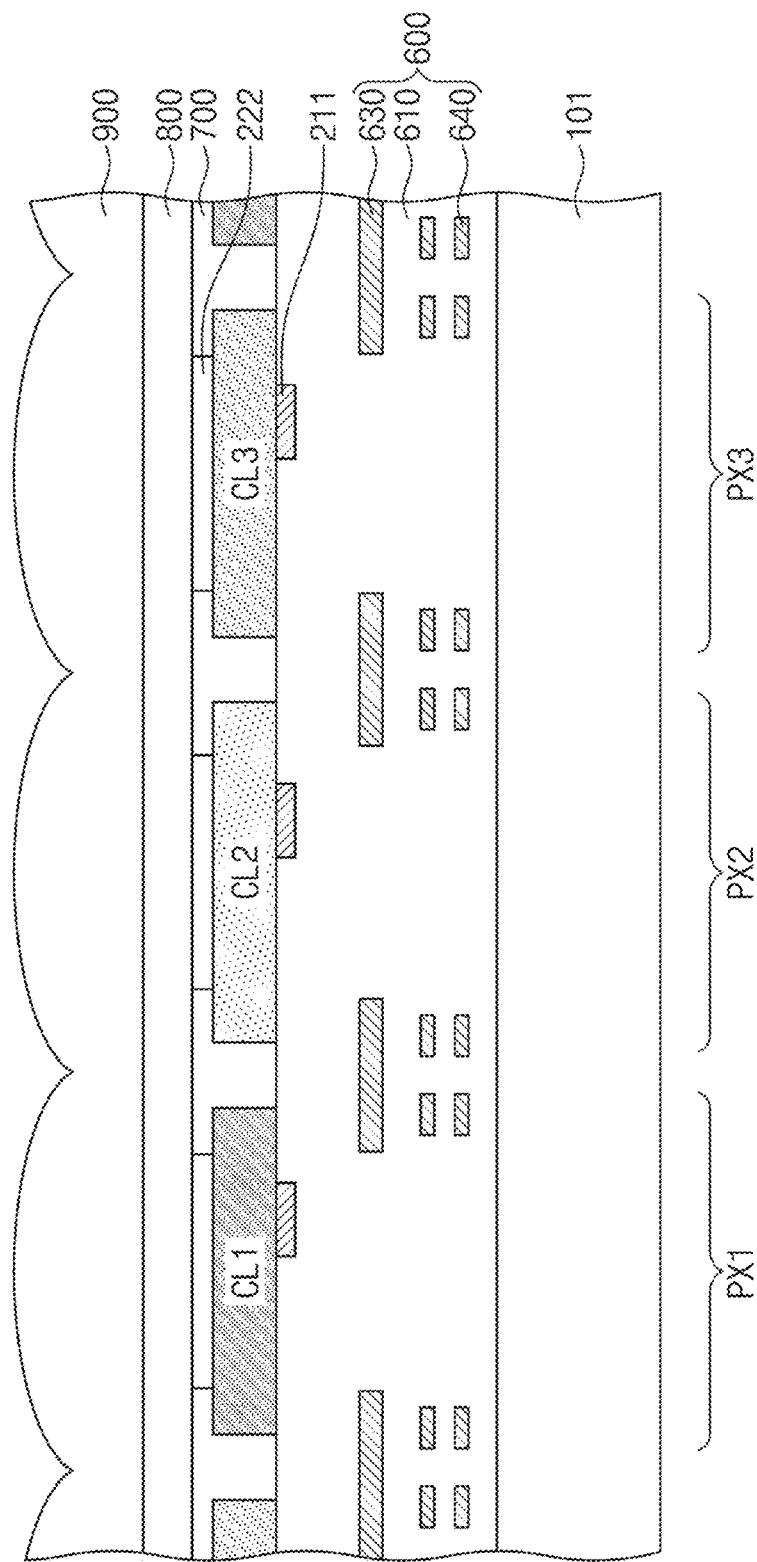
FIG. 11 is a diagram for explaining an image sensor according to embodiments.

FIG. 11 is a diagram for explaining an image sensor according to embodiments.

Referring to FIG. 11, the image sensor may include a semiconductor substrate 101, a wiring layer 600, first electrodes 211, color-selective photoactive layers CL1, CL2 and CL3, second electrodes 222, a protective layer 800, and a microlens layer 900.

The semiconductor substrate 101, for example, may include silicon or silicon-germanium. The semiconductor substrate 101 may have a first pixel region PX1, a second pixel region PX2, and a third pixel region PX3 from a planar perspective. The semiconductor substrate 101 may not be provided with a separate photodiode.

The wiring layer 600 may be disposed on the semiconductor substrate 101. The wiring layer 600 may include an insulating layer 610, wiring patterns 640, and a light-shielding pattern 630. The insulating layer 610 may be a single layer or a multilayer. The wiring patterns 640 may be provided in the insulating layer 610. The wiring patterns 640 may include a conductive material such as a metal. The insulating layer 610 may be provided with the light-shielding pattern 630. The light-shielding pattern 630 may include a metal. The light-shielding pattern 630 may have a long axis extending horizontally.

The first electrodes 211 may be provided in the wiring layer 600, and exposed on the upper surface of the wiring layer 600. The first electrodes 211 may be respectively provided in a pixel region PX1, a second pixel region PX2, and a third pixel region PX3. The first electrodes 211 may be pixel electrodes.

The color selective photoactive layers CL1, CL2, CL3 may be disposed on the wiring layer 600. The color selective photoactive layers CL1, CL2, CL3 may include a first color selective photoactive layer CL1, a second color selective photoactive layer CL2, and a third color selective photoactive layer CL3. For example, the first color selective photoactive layer CL1, the second color selective photoactive layer CL2, and the third color selective photoactive layer CL3 may be a red selective photoactive layer, a green selective photoactive layer, and a blue selective photoactive layer, respectively. The first color selective photoactive layer CL1, the second color selective photoactive layer CL2, and the third color selective photoactive layer CL3 may be provided in the first pixel region PX1, the second pixel region PX2, and the third pixel region PX3, respectively. The first color selective photoactive layer CL1, the second color selective photoactive layer CL2, and the third color selective photoactive layer CL3 may be arranged to be laterally spaced apart from each other. The first color selective photoactive layer CL1, the second color selective photoactive layer CL2, and the third color selective photoactive layer CL3 may be connected to the corresponding first electrodes 211, respectively. For example, the first color selective photoactive layer CL1 may include a photosensitive material and a first color selective organic semiconductor material. The second color selective photoactive layer may include a photosensitive material and a second color selective organic semiconductor material. The third color selective photoactive layer may include a photosensitive material and a third color selective organic semiconductor material. The first color may be red, the second color may be blue, and the third color may be green. The first color selective organic semiconductor may be different from the second color organic semiconductor material and the third color selective organic semiconductor material. The second color selective organic semiconductor material may be different from the third color selective organic semiconductor material. The first color selective photoactive layer CL1, the second color selective photoactive layer CL2, and the third color selective photoactive layer CL3 may include the same photosensitive material. Although not shown, a near-infrared selective photoactive layer may be further provided.

The second electrodes 222 may be respectively disposed on the first color selective photoactive layer CL1, the second color selective photoactive layer CL2, and the third color selective photoactive layer CL3. The second electrodes 222 may be electrically connected to the first color selective photoactive layer CL1, the second color selective photoactive layer CL2, and the third color selective photoactive layer CL3, respectively. The voltage applied to the second electrodes 222 may be different from the voltage applied to the first electrodes 211. When the first electrodes 211 are anodes, the second electrodes 222 may be cathodes. When the first electrodes 211 are cathodes, the second electrodes 222 may be anodes. The second electrodes 222 may be transparent electrodes.

The protective layer 800 may be disposed on the second electrodes 222. The protective layer 800 may have insulating characteristics. The protective layer 800 may include, for example, an organic material such as polymer. The protective layer 800 may be transparent.

A buffer layer 700 may be disposed between the wiring layer 600 and the protective layer 800, and cover the sidewalls of the color selective photoactive layers CL1, CL2, CL3, and the sidewalls of the second electrodes 222. The buffer layer 700 may include an insulating material.

The microlens layer 900 may be disposed on the protective layer 800. The microlens layer 900 may collect light. The microlens layer 900 may be transparent.

Hereinafter, with reference to the experimental examples of the inventive concept, the production and analysis results of the photosensitive material will be described. In reaction formulae below, Ph means phenyl, Bu means butyl, and THF means tetrahydrofuran.

1. Preparation of Intermediate Material (1) Preparation of Intermediate Material A A reaction represented by Reaction Formula 2A is carried out to synthesize an intermediate material A.

[Reaction Formula 2A]

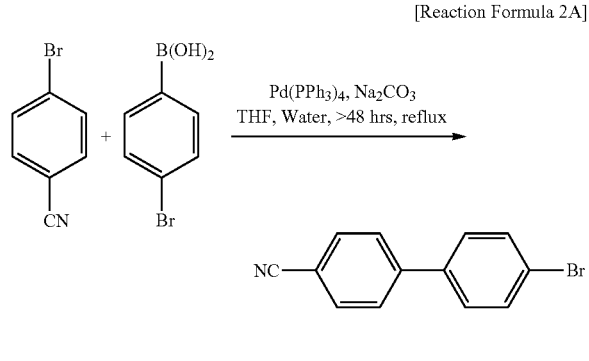

(2) Preparation of Intermediate Material B

A reaction represented by Reaction Formula 2B is carried out to synthesize an intermediate material B.

[Reaction Formula 2B]

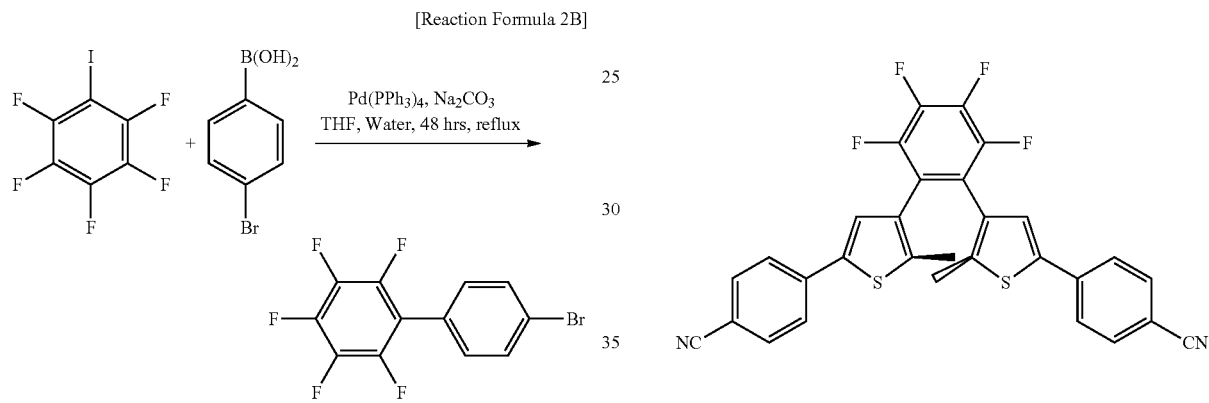

In Reaction Formula 2A, a commercially available product obtained from Sigma Aldrich is used as a reactant, Iodopentafluorobenzene (CAS number: 827-15-6).

2. Preparation and Analysis of Photosensitive Material (1) Preparation and Analysis of Material Represented by Chemical Formula 1A (Experimental Example 1A)

A reaction represented by Reaction Formula 3A is carried out to obtain the final product.

[Reaction Formula 3A]

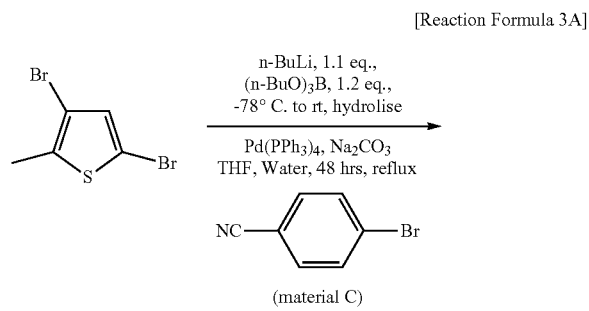

(material C)

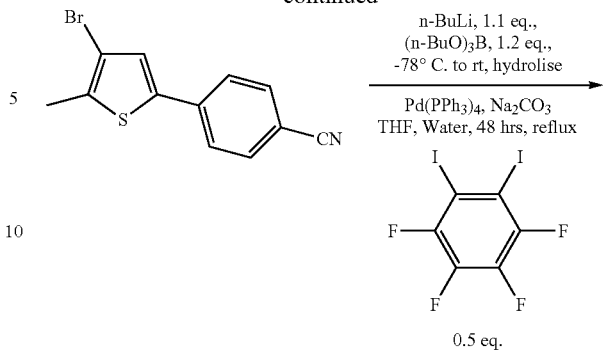

In Reaction Formula 3A, starting materials, which are 3,5-dibromo-2-methylthiophene (CAS number: 29421-73-6), material C (CAS number:623-00-7, obtained from Sigma Aldrich), and Iodpmentafluorobenzene (CAS number: 827-15-6, obtained from Sigma Aldrich), employ commercially available products.

Analysis of Nuclear Magnetic Resonance (NMR)

Figure 12A:
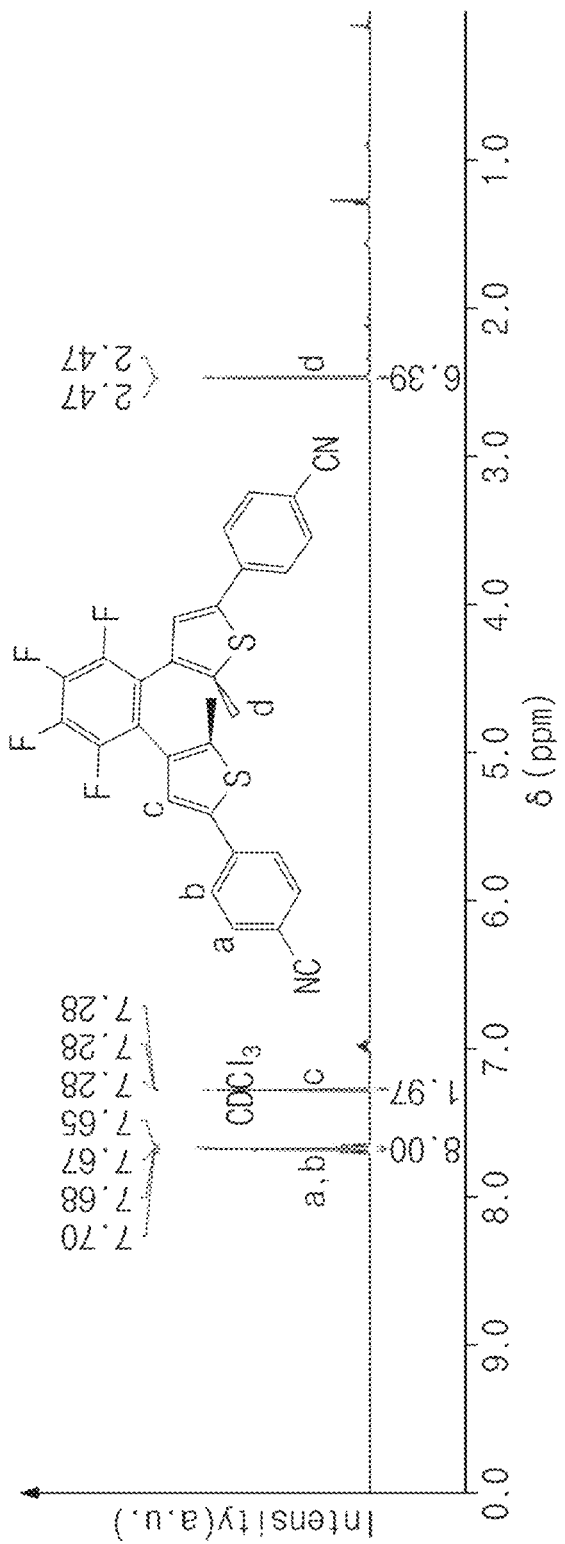
FIG. 12A is a $^1$H nuclear magnetic resonance spectrum ($^1$H NMR) result of the final product according to Experimental Example 1A.
Figure 12B:
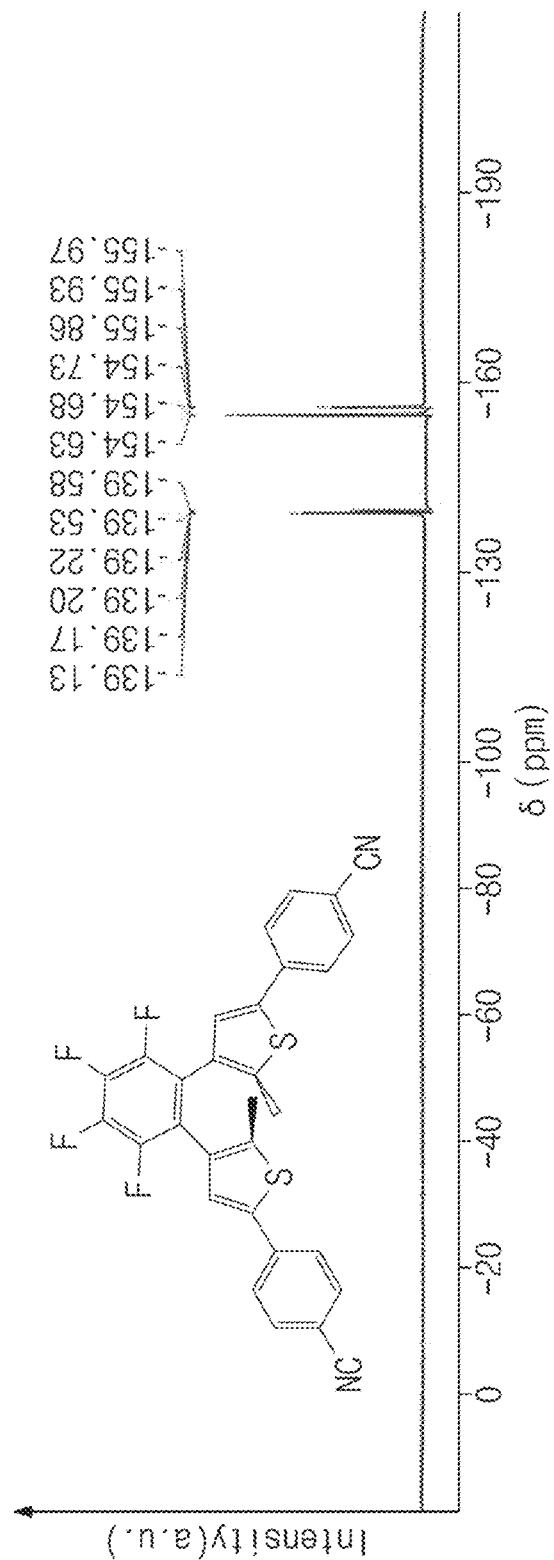
FIG. 12B is a $^{19}$F nuclear magnetic resonance spectrum ($^{19}$F NMR) result of the final product according to Experimental Example 1A.
Figure 12C:
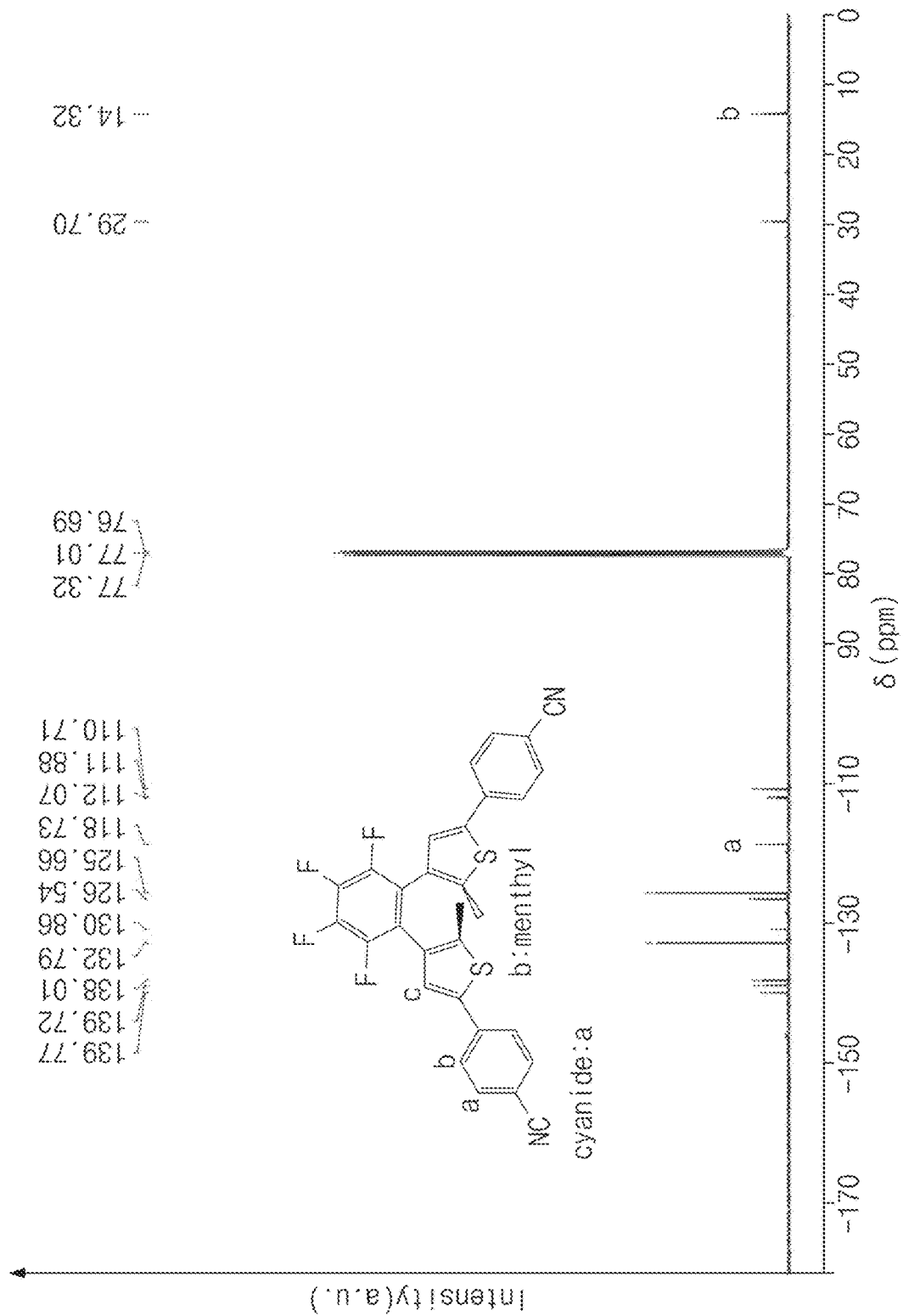
FIG. 12C is a $^{13}$C nuclear magnetic resonance spectrum ($^{13}$C NMR) result of the final product according to Experimental Example 1A.

FIG. 12A is a $^1$H nuclear magnetic resonance spectrum ($^1$H NMR) result of the final product according to Experimental Example 1A. FIG. 12B is a $^{19}$F nuclear magnetic resonance spectrum (19F NMR) result of the final product according to Experimental Example 1A. FIG. 12C is a 13C nuclear magnetic resonance spectrum ($^{13}$C NMR) result of the final product according to Experimental Example 1A. In FIGS. 12A, 12B, and 12C, the x-axis denotes δ (ppm), and the y-axis denotes an intensity (unit: an arbitrary unit, A.U.).

Referring to FIGS. 12A to 12C, it may be confirmed that the synthesized final product is a material represented by Chemical Formula 1A.

(2) Preparation and Analysis of Material Represented by Chemical Formula 1B

A reaction represented by Reaction Formula 3B is carried out to obtain the final product.

[Reaction Formula 3B]

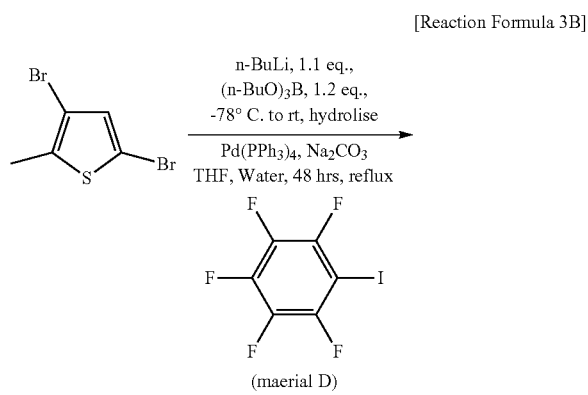

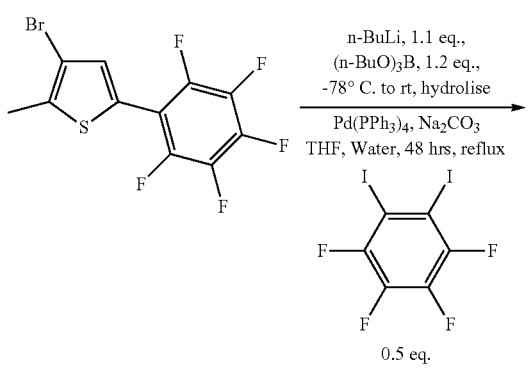

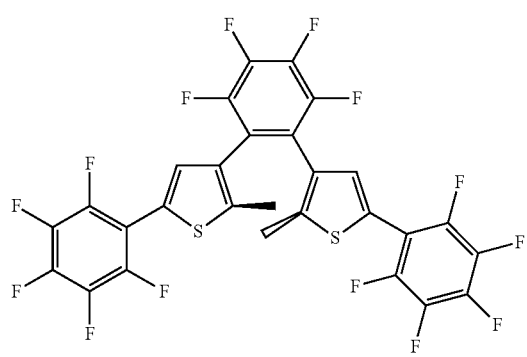

In Reaction Formula 3B, starting materials, which are 3,5-dibromo-2-methylthiophene (CAS number: 29421-73-6), material D (CAS number:2708-97-6, obtained from Sigma Aldrich), and Iodpmentafluorobenzene (CAS number: 827-15-6), employ commercially available products.

(3) Preparation and Analysis of Material Represented by Chemical Formula 1C

A reaction represented by Reaction Formula 3C is carried out to obtain the final product.

[Reaction Formula 3C]

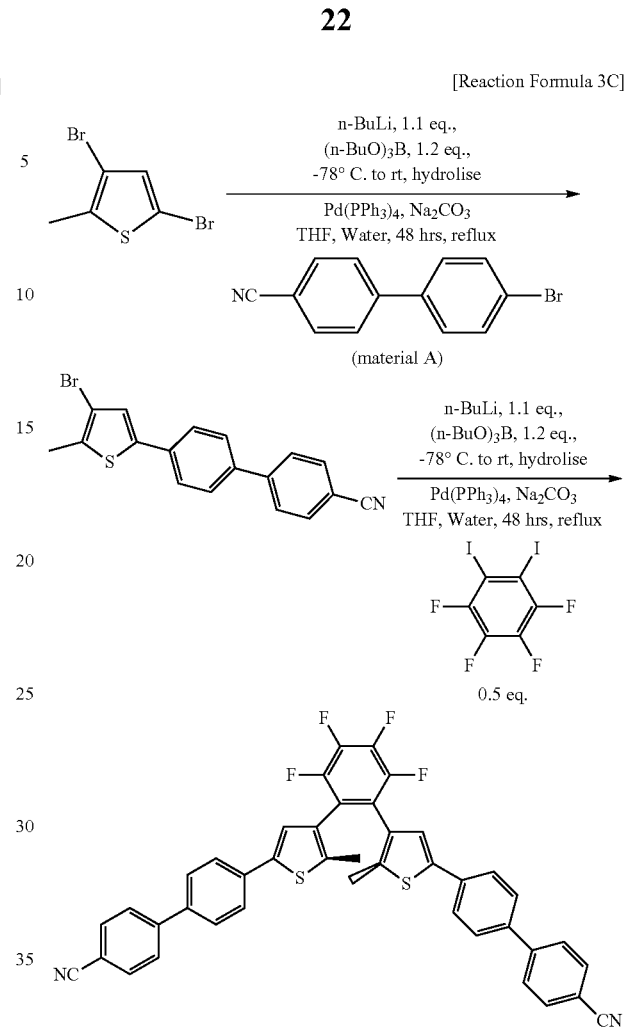

In Reaction Formula 3C, starting materials, which are 3,5-dibromo-2-methylthiophene (CAS number: 29421-73-6), and Iodpmentafluorobenzene (CAS number: 827-15-6), employ commercially available products, and the intermediate material A, which has been synthesized in advance, was used as material A.

Analysis of Nuclear Magnetic Resonance (NMR)

Figure 13A:
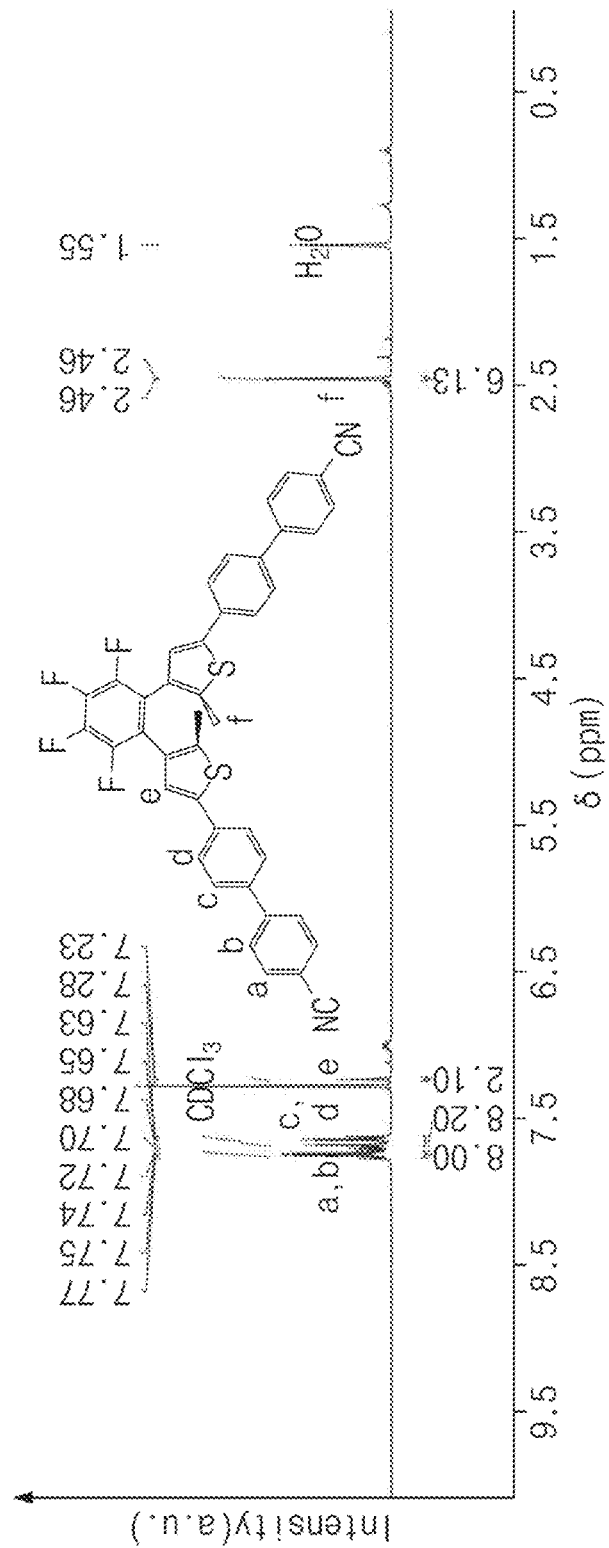
FIG. 13A is a $^1$H nuclear magnetic resonance spectrum ($^1$H NMR) result of the final product according Experimental Example 1C.
Figure 13B:
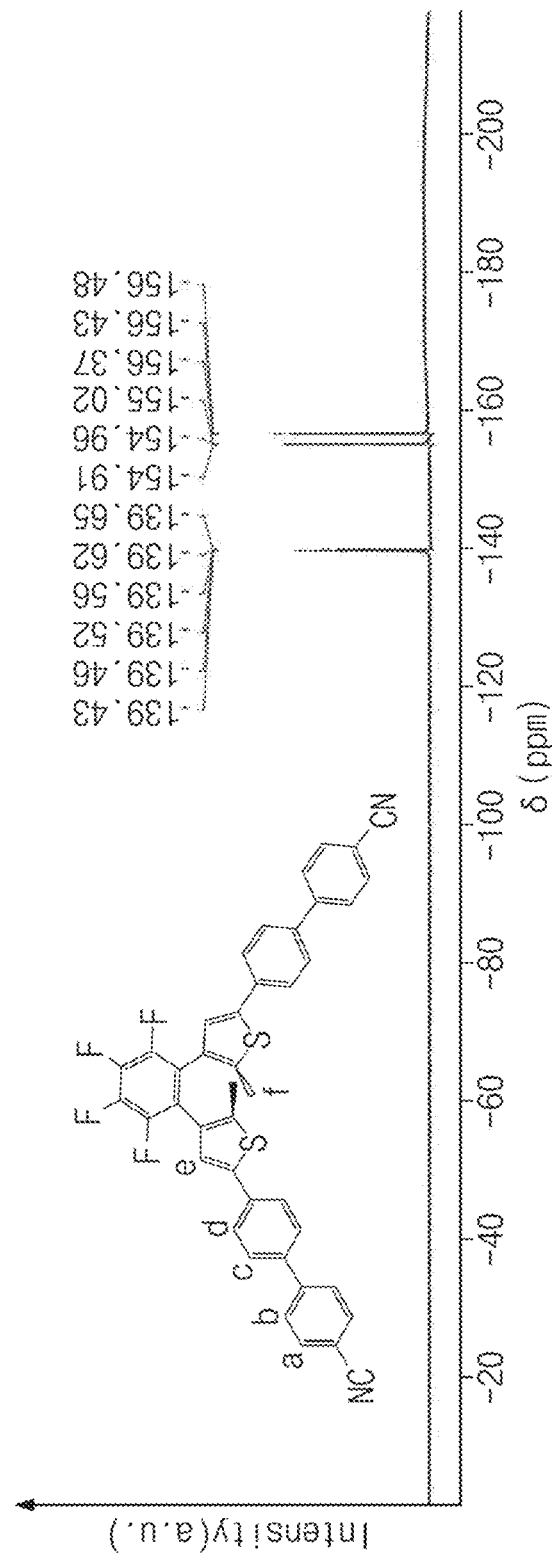
FIG. 13B is a $^{19}$F nuclear magnetic resonance spectrum ($^{19}$F NMR) result of the final product according to Experimental Example 1C.
Figure 13C:
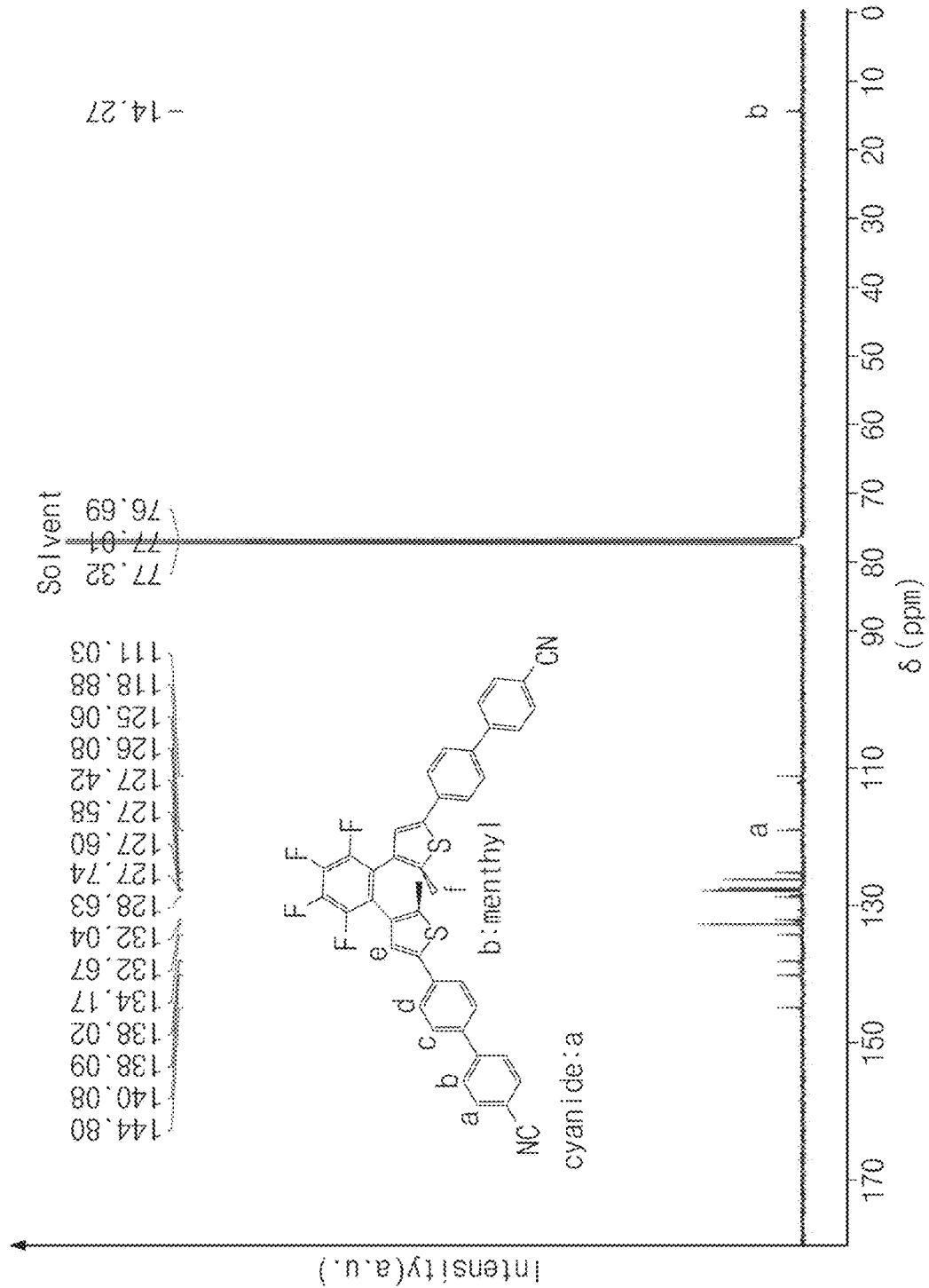
FIG. 13C is a $^{13}$C nuclear magnetic resonance spectrum ($^{13}$C NMR) result of the final product according to Experimental Example 1C.

FIG. 13A is a $^1$H nuclear magnetic resonance spectrum ($^1$H NMR) result of the final product according to Experimental Example 1C. FIG. 13B is a $^{19}$F nuclear magnetic resonance spectrum ($^{19}$F NMR) result of the final product according to Experimental Example 1C. FIG. 13C is a $^{13}$C nuclear magnetic resonance spectrum ($^{13}$C NMR) result of the final product according to Experimental Example 1C. In FIGS. 13A, 13B, and 13C, the x-axis denotes δ (ppm), and the y-axis denotes an intensity (unit: an arbitrary unit, A.U.).

Referring to FIGS. 13A to 13C, it may be confirmed that the synthesized final product is a material represented by Chemical Formula 1C.

(4) Preparation and Analysis of Material Represented by Chemical Formula 1D

A reaction represented by Reaction Formula 3D is carried out to obtain the final product.

[Reaction Formula 3D]

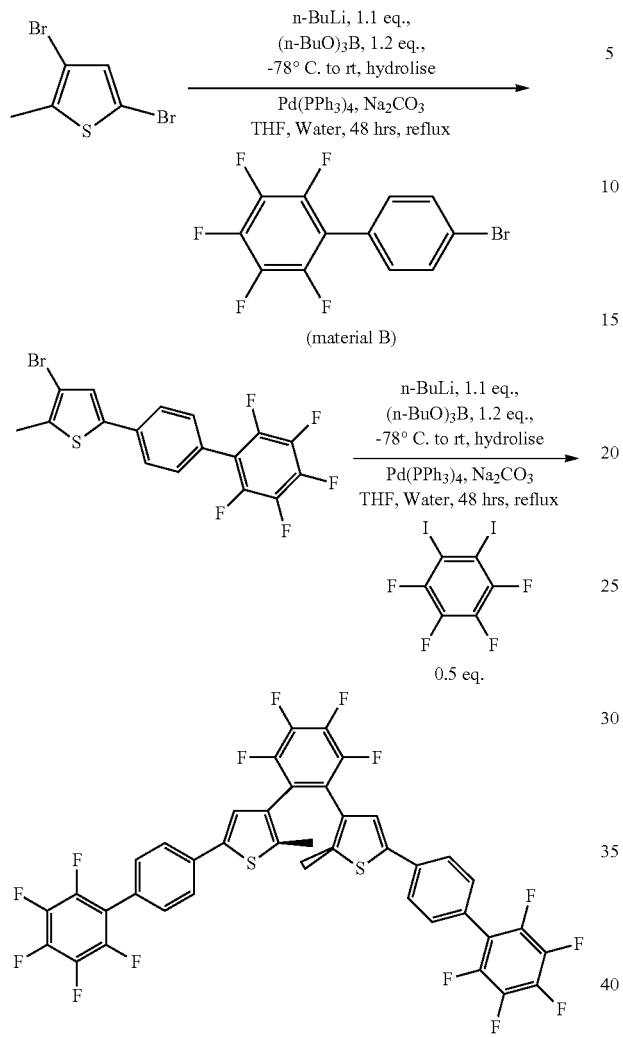

In Reaction Formula 3D, starting materials, which are 3,5-dibromo-2-methylthiophene (CAS number: 29421-73-6), employ commercially available products, and the intermediate material B, which has synthesized in advance, was used as material B.

According to embodiments of the inventive concept, a photodetector may function as a photodiode under a first incidence condition, and may function as a photoconductor under a second incidence condition. Light under the second incidence condition has the same wavelength as but a larger intensity than light under the first incidence condition. Accordingly, the photodetector may exhibit a low dark-current characteristic and a high external quantum efficiency.

The detailed description of the inventive concept is not intended to limit the inventive concept to the disclosed embodiment, and may be used in various other combination, changes, and environments without departing from the gist of the inventive concept. The appended claims should be interpreted as including other embodiments.

What is claimed is:

1. A photodetector comprising a photoactive layer having a photocurrent density of at most about $10^{-6}$ A/cm$^2$ under a first incidence condition, and having a photocurrent density of at least about $10^{-4}$ A/cm$^2$ under a second incidence condition,
wherein a wavelength of light under the second incidence condition is the same as a wavelength of light under the first incidence condition, and an intensity of light under the second incidence condition is greater than an intensity of light under the first incidence condition,
wherein the photoactive layer includes a photosensitive material, and the photosensitive material has a first state represented by Chemical Formula 1, and a second state in which a carbon to which Ra is bonded and a carbon to which Ra is bonded, in Chemical Formula 1, are connected to each other to form a ring structure,

[Chemical Formula 1]

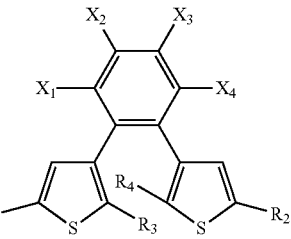

wherein, in Chemical Formula 1, $R_1$ and $R_2$ each independently include a substituted or unsubstituted aromatic ring compound having 5 to 20 carbon atoms, $R_3$ and $R_4$ are each independently an alkyl group having 1 to 3 carbon atoms, $X_1$, $X_2$, $X_3$, and $X_4$ are each independently hydrogen or a halogen element, and at least one of $X_1$, $X_2$, $X_3$, or $X_4$ includes a halogen element, and
wherein $R_1$ and $R_2$ are each independently a cyano (—CN)-substituted aromatic ring compound having 5 to 20 carbon atoms, or a halogen-substituted aromatic ring compound having 5 to 20 carbon atoms.

2. The photodetector of claim 1, wherein the intensity of the light under the first incidence condition is at most about $10^{-3}$ W/cm$^2$.

3. The photodetector of claim 1, wherein the photoactive layer further includes an organic semiconductor material.

4. The photodetector of claim 1, wherein a lowest unoccupied molecular orbital (LUMO) energy level of the photosensitive material in the second state is different from a LUMO energy level of the photosensitive material in the first state.

5. The photodetector of claim 4, wherein the LUMO energy level of the photosensitive material in the first state is at least about −3 eV, the LUMO energy level of the photosensitive material in the second state is less than −3 eV, and the photosensitive material in the first state has an absorption peak of at least about 300 nm.

6. The photodetector of claim 1, further comprising:
a first electrode disposed on a first surface of the photoactive layer; and
a second electrode disposed on a second surface of the photoactive layer,
wherein the second surface of the photoactive layer faces the first surface.

7. The photodetector of claim 6, wherein the photoactive layer and the first electrode forms a Schottky junction under the first incidence condition, and the photoactive layer and the first electrode forms an ohmic junction under the second incidence condition.

8. A photosensitive material having:
a first state represented by Chemical Formula 1; and
a second state in which a carbon to which $R_3$ is bonded and a carbon to which $R_4$ is bonded, in Chemical Formula 1, are connected to each other to form a ring structure,
wherein the photosensitive material has a LUMO energy level of at least about −3 eV and an absorption peak of at least about 300 nm in the first state, and has a LUMO energy level of less than about −3 eV in the second state,

[Chemical Formula 1]

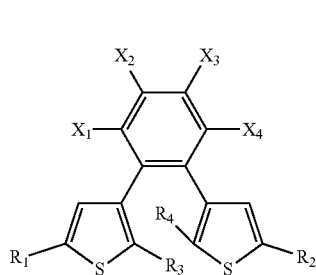

wherein, in Chemical Formula 1, $R_1$ and $R_2$ each independently include a substituted or unsubstituted aromatic ring compound having 5 to 20 carbon atoms, $R_3$ and $R_4$ are each independently an alkyl group having 1 to 3 carbon atoms, $X_1$, $X_2$, $X_3$, and $X_4$ are each independently hydrogen or a halogen element, and at least one of $X_1$, $X_2$, $X_3$, or $X_4$ includes a halogen element, and wherein $R_1$ and $R_2$ in Chemical Formula 1 are each independently a cyano (—CN)-sustained aromatic ring compound having 5 to 20 carbon atoms, or a halogen-substituted aromatic ring compound having 5 to 20 carbon atoms.

9. The photosensitive material of claim 8, wherein the second state is represented by Chemical Formula 2,

[Chemical Formula 2]

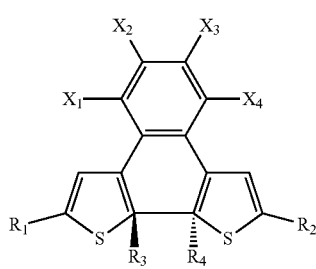

wherein, in Chemical Formula 2, $R_1$ and $R_2$ each independently include a substituted or unsubstituted aromatic ring compound having 5 to 20 carbon atoms, $R_3$ and $R_4$ are each independently an alkyl group having 1 to 3 carbon atoms, $X_1$, $X_2$, $X_3$, and $X_4$ are each independently hydrogen or a halogen element, and at least one of $X_1$, $X_2$, $X_3$, or $X_4$ includes a halogen element.

10. The photosensitive material of claim 8, wherein a material represented by Chemical Formula 1 is represented by any one among Chemical Formula 1A, Chemical Formula 1B, and Chemical Formula 1D,

[Chemical Formula 1A]

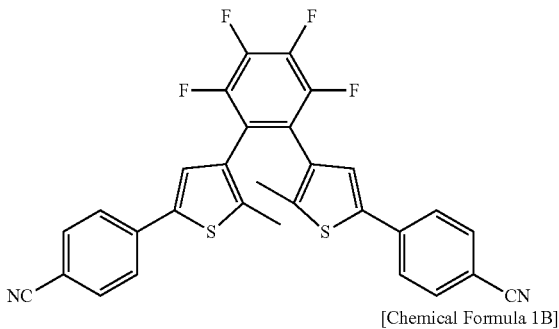

[Chemical Formula 1B]

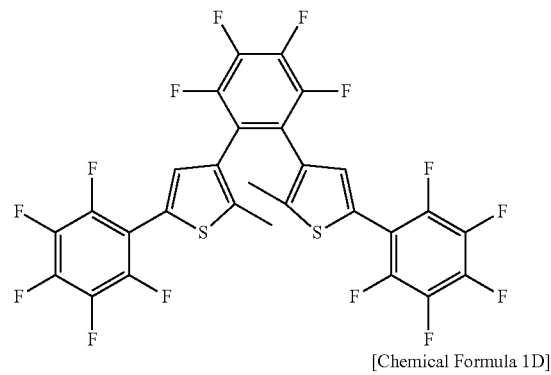

[Chemical Formula 1D]

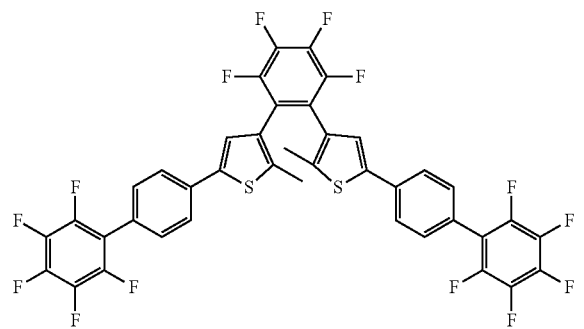

11. The photosensitive material of claim 8, wherein a material represented by Chemical Formula 1 is represented by Chemical Formula 1C

[Chemical Formula 1C]

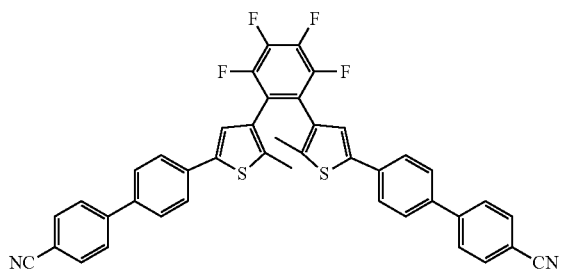

* * * * *